(12) United States Patent
Nilsson et al.

(10) Patent No.: US 8,466,158 B2
(45) Date of Patent: *Jun. 18, 2013

(54) CYSTEINE PROTEASE INHIBITORS

(75) Inventors: Magnus Nilsson, Huddinge (SE); Lourdes Salvador Odén, Huddinge (SE); Pia Kahnberg, Huddinge (SE); Urszula Grabowska, Essex (GB)

(73) Assignee: Medivir AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,787

(22) Filed: May 10, 2012

(65) Prior Publication Data

US 2012/0220602 A1     Aug. 30, 2012

Related U.S. Application Data

(62) Division of application No. 12/986,830, filed on Jan. 7, 2011, now Pat. No. 8,198,283, which is a division of application No. 12/145,987, filed on Jun. 25, 2008, now Pat. No. 7,893,067.

(60) Provisional application No. 60/929,437, filed on Jun. 27, 2007.

(30) Foreign Application Priority Data

Dec. 20, 2007  (EP) .................................... 07123771

(51) Int. Cl.
    *A61K 31/496* (2006.01)
(52) U.S. Cl.
    USPC ...................... 514/254.02; 544/369
(58) Field of Classification Search
    None
    See application file for complete search history.

(56) References Cited

U.S. PATENT DOCUMENTS

| | | | |
|---|---|---|---|
| 7,893,067 B2 | 2/2011 | Nilsson et al. | |
| 8,008,290 B2 | 8/2011 | Quibell et al. | |
| 8,198,283 B2 * | 6/2012 | Nilsson et al. | 514/254.02 |
| 2010/0010009 A1 | 1/2010 | Quibell et al. | |

FOREIGN PATENT DOCUMENTS

| WO | WO-98/50533 A1 | 11/1998 |
|---|---|---|
| WO | WO-01/58886 A1 | 8/2001 |
| WO | WO-02/057270 A1 | 7/2002 |
| WO | WO-02/088106 A2 | 11/2002 |
| WO | WO-2005/056529 A1 | 6/2005 |
| WO | WO-2005/065578 A2 | 7/2005 |
| WO | WO-2005/066159 A1 | 7/2005 |
| WO | WO-2005/066180 A1 | 7/2005 |
| WO | WO-2007/006716 A1 | 1/2007 |
| WO | WO-2008/007127 A1 | 1/2008 |

OTHER PUBLICATIONS

Delaisse et al. Clinica Chimica Acta, vol. 291, p. 223-234 (2000).*
Copending U.S. Appl. No. 10/584,930 (Nilsson et al.)—filed Mar. 31, 2008.
International Search Report (Form PCT/ISA/210) for PCT/GB2005/050003, Oct. 5, 2005.
Written Opinion of The International Searching Authority (Forms PCT/ISA/237) for PCT/GB2005/050003, Oct. 5, 2005.
Biskebing, Expert Opinion on Investigational Drugs, vol. 12, pp. 611-621 (2003).
Cai et al. Expert Opinion on Therapeutic Patents, vol. 15, pp. 33-48 (2005).
Third Part Observations filed on behalf of Amura Therapeutics Limited, Jan. 5, 2009.
Applicant's Response to Examination Report in Corresponding European Application, Mar. 2, 2009.
Watts, et al., "Functionalised 2,3-dimethyl-3-aminotetrahydrofuran-4-one and N-(3-oxo-hexahydrocyclcopenta[b]furan-3a-yl)acylamide based scaffolds: synthesis and cysteinyl proteinase inhibition", Bioorganic and Medicinal Chemistry, 2004, 12:2903-2925.
Quibell, "Bicyclic peptidomimetic tetrahyrofurol[3,2-b]pyrrol-3-one and hexahydrofuro[3,2-b]pyridine-3-one scaffolds: synthesis and cysteinyl proteinase inhibition", Bioorganic and Medicinal Chemistry, 2004, 12:5689-5710.
Wolfe et al., Scope and Limitations of the Pd/BINAP-Catalyzed Amination of Aryl Bromides, J. Org. Chem, 2000, vol. 65, pp. 1144-1157.
Banker et al., "Modern Pharmaceutics" 3rd Ed., pp. 596, 1996.
Wolff, M. E., "Burger's Medicinal Chemistry" 5th Ed. Part 1, pp. 975-977, 1995.

* cited by examiner

*Primary Examiner* — Emily Bernhardt
(74) *Attorney, Agent, or Firm* — Birch, Stewart, Kolasch & Birch, LLP

(57) ABSTRACT

Compounds of the formula II:

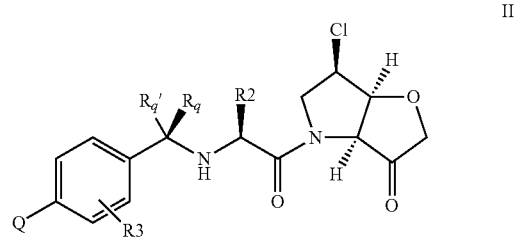

wherein
$R^2$ is the side chain of leucine, isoleucine, cyclohexylglycine, O-methyl threonine, 4-fluoroleucine or 3-methoxyvaline;
$R^3$ is H, methyl or F;
Rq is trifluoromethyl and Rq' is H or Rq and Rq' define keto;
Q is a p-($C_1$-$C_6$alkylsulphonyl)phenyl- or an optionally substituted 4-($C_1$-$C_6$alkyl)piperazin-1-yl-thiazol-4-yl-moiety have utility in the treatment of disorders characterized by inappropriate expression or activation of cathepsin K, such as osteoporosis, osteoarthritis, rheumatoid arthritis or bone metastases.

2 Claims, No Drawings

CYSTEINE PROTEASE INHIBITORS

This application is a Divisional of application Ser. No. 12/986,830 filed on Jan. 7, 2011, which is a Divisional of application Ser. No. 12/145,987 (now U.S. Patent No. 7,893, 067) filed on Jun. 25, 2008, and for which priority is claimed under 35 U.S.C. §120; and this application claims priority of U.S. Provisional Application No. 60/929,437 filed on Jun. 27, 2007 and European Application No.: EP07123771 filed on Dec. 20, 2007 under 35 U.S.C. §119; the entire contents of each of which are hereby incorporated by reference.

FIELD OF THE INVENTION

This invention relates to inhibitors of cysteine proteases, especially those of the papain superfamily. The invention provides novel compounds useful in the prophylaxis or treatment of disorders stemming from misbalance of physiological proteases such as cathepsin K.

DESCRIPTION OF THE RELATED ART

The papain superfamily of cysteine proteases is widely distributed in diverse species including mammals, invertebrates, protozoa, plants and bacteria. A number of mammalian cathepsin enzymes, including cathepsins B, F, H, K, L, O and S, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, III et seq and cysteine proteases from *Pneumocystis carinii, Trypanosoma cruzi* and *brucei, Crithidia fusiculata, Schistosoma* spp.

The inappropriate regulation of cathepsin K has been implicated in a number of disorders including osteoporosis, gingival diseases such as gingivitis and periodontitis, Paget's disease, hypercalcaemia of malignancy and metabolic bone disease. In view of its elevated levels in chondroclasts of osteoarthritic synovium, cathepsin K is implicated in diseases characterised by excessive cartilage or matrix degradation, such as osteoarthritis and rheumatoid arthritis.

It is likely that treatment of bone and cartilage disorders such as osteoarthritis and osteoporosis will require life-long administration of a cathepsin K inhibitor, often to a patient population within or nearing the geriatric phase. This places unusually high requirements on the ease of administration of drugs intended for such disorders. For example attempts are underway to stretch the dosage regimes of the current osteoporosis drugs of the bisphosphonate class to weekly or longer administration regimes to aid compliance. However, even with improved dosing, other side effects of the bisphosphonates, remain. Bisphosphonates block bone turnover rather than attenuate it as a cathepsin K inhibitor does. For healthy bone it is important to maintain the remodelling process which bisphosphonates block completely. In addition, bis-phosphonates have a very long half-life in bone so if effects such as osteonecrosis of the jaw manifest themselves, it is impossible to remove the bisphosphonate from the bone. In contrast, cathepsin K inhibitors typically have a fast onset and off rate mode of action, which means that if a problem was to be identified, dosing could be halted and there would be no build up of the inhibitor in the bone matrix.

There is thus a desire for alternative osteoporosis and osteoarthritis drugs with superior pharmacokinetic and/or pharmacodynamic properties.

International patent application no WO02/057270 discloses compounds of the formula IA:

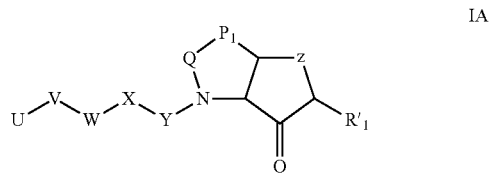

where UVWXY broadly corresponds to the P3 and P2 (these expressions are explained below) of dipeptide cysteine protease inhibitors, Z is inter alia O, S, methylene or —NR—, $R'_1$, is alkyl, alkylaryl etc and $P_1$ and Q are each, inter alia, methylene. Although the generic disclosure in this patent application postulates a very broad range of substituents on $P_1$ and Q, none are individualised or exemplified and no guidance is provided on their synthesis. Indeed—the only synthesis suggestions provided in WO02/05720 do not allow for substitution at $P_1$ or Q at all. The compounds are alleged to be useful, inter alia, for the treatment of protozoal infections such as trypanosomes.

Example 9 of international patent application no WO2005/066180 discloses, inter alia, a compound of the formula IB:

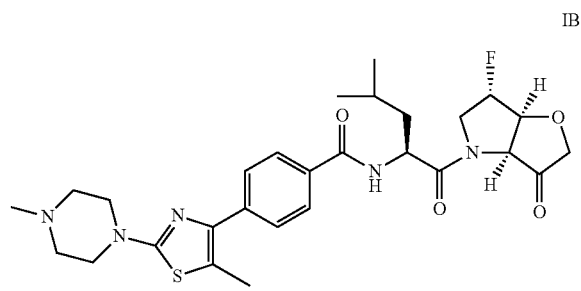 [SMILES: Cc1sc(N2CCN(C)CC2)nc1-c1ccc(C(=O)N[C@@H](CC(C)C)C(=O)N2C[C@H](F)[C@H]3OCC(=O)[C@H]32)cc1]

The compound is an active inhibitor of cathepsin K, but, as shown below, further modification of the structure yields improvements as regards to pharmacokinetics and/or pharmacodynamics, notably enhanced stability in whole blood, and therefore a better exposure.

WO2008/007127, which was unpublished at the priority date of the present application, discloses compounds of the formula IC:

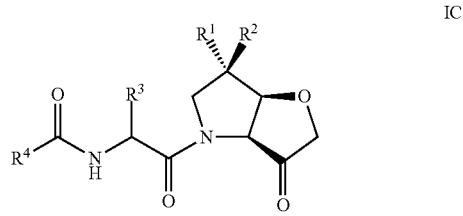

which are described as cysteine protease inhibitors, in particular, inhibitors of cathepsin K.

BRIEF DESCRIPTION OF THE INVENTION

According to the present invention there is provided a compound of the Formula II:

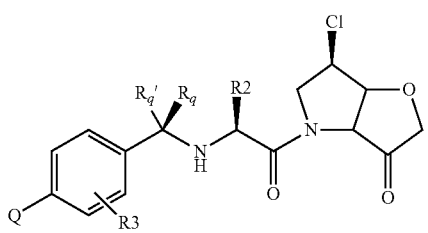

II wherein
R² is the side chain of leucine, isoleucine, cyclohexylglycine, O-methyl threonine, 4-fluoroleucine or 3-methoxyvaline;
R³ is H, methyl or F;
Rq is CF₃ with the indicated stereochemistry and Rq' is H; or Rq and Rq' together define keto;
Q is

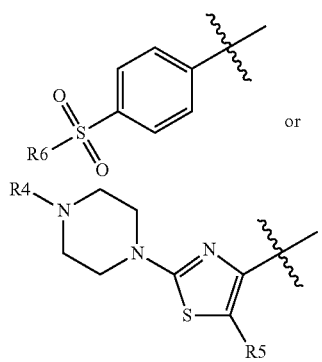

wherein
R⁴ is $C_1$-$C_6$ alkyl;
R⁵ is H, methyl or F;
R⁶ is $C_1$-$C_6$ alkyl;
or a pharmaceutically acceptable salt, prodrug or N-oxide thereof.

In accordance with one aspect of the invention there is provided enantiomeric compounds of the formula:

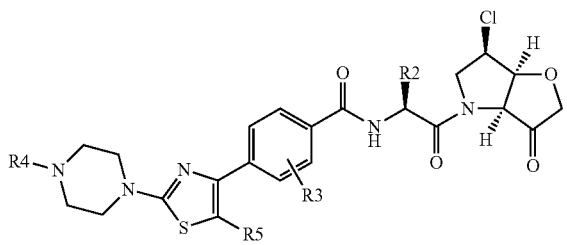

IIa wherein
R² is the side chain of leucine, isoleucine, cyclohexylglycine, O-methyl threonine, 4-fluoroleucine or 3-methoxyvaline;
R³ is H, methyl or F;

R⁴ is $C_1$-$C_6$ alkyl, preferably methyl;
R⁵ is H, methyl or F;
or a pharmaceutically acceptable salt, N-oxide or hydrate thereof.

An alternative embodiment of the invention comprises compounds or pharmaceutically acceptable salts, N-oxides or hydrates of compounds of the formula IIb

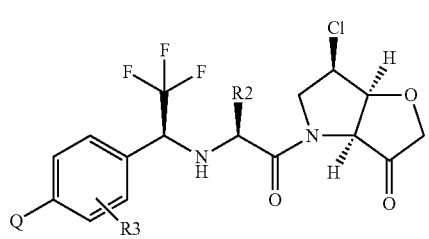

IIb where R² and R³ are as defined above and Q is the N-alkyl-piperazinyl-thiazolyl moiety defined in formula IIa or 4-($C_1$-$C_4$ alkyl)sulphonylphenyl moiety, as described in WO 07/006,716, for example a compound of the formula:

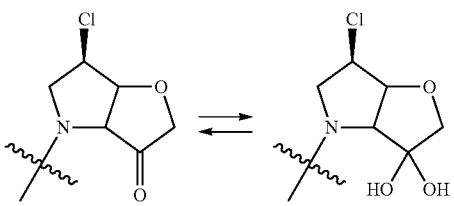 [SMILES: *N1C[C@@H](Cl)C2OCC(=O)C21 ; *N1C[C@@H](Cl)C2OCC(O)(O)C21]

The expression "$C_{1-6}$ alkyl" denotes an alkyl chain having between one and six carbon atoms (for example, a $C_{1-4}$ alkyl group, or a $C_{1-3}$ alkyl group). Alkyl groups may be straight chain or branched. Suitable $C_{1-6}$ alkyl groups include, for example, methyl, ethyl, propyl (e.g. n-propyl and isopropyl), butyl (e.g n-butyl, iso-butyl, sec-butyl and tert-butyl), pentyl (e.g. n-pentyl) and hexyl (e.g. n-hexyl). An alkyl group of particular interest is methyl.

It will be appreciated that the compounds of the invention can exist as hydrates, such as those of the partial formulae:

and the invention extends to all such alternative forms.

In a favoured embodiment of the invention R² is the side chain of leucine, isoleucine, O-methyl threonine, 4-fluoroleucine or 3-methoxyvaline Currently preferred values of $R^2$, include those embodied by the partial structures:

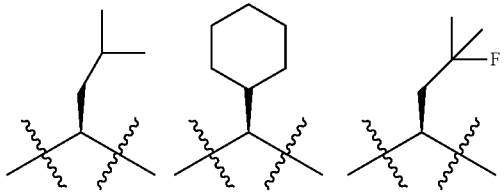

especially the value of $R^2$ corresponding to the side chain of L-leucine.

The embodiments of the paragraph immediately above are advantageously applied to compounds wherein $R^3$ or $R^5$ are fluoro.

Typically variable $R^3$ as methyl or fluoro, if present, is located at the meta position relative to the benzylic amide bond, as shown below in the partial structure:

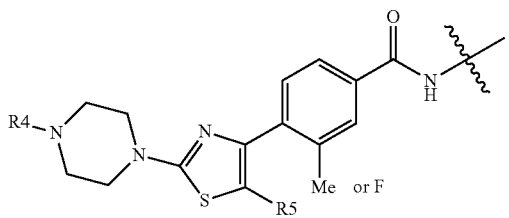

A representative compound of this embodiment has the formula:

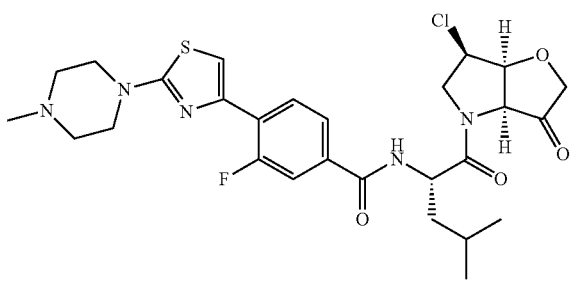 [SMILES: CC(C)C[C@H](NC(=O)c1ccc(-c2csc(N3CCN(C)CC3)n2)c(F)c1)C(=O)N1C[C@@H](Cl)[C@H]2OCC(=O)[C@H]21]

In certain embodiments of the invention, $R^5$ is F, especially when $R^3$ is H and/or $R^4$ is methyl. Favoured compounds within this embodiment have an $R^2$ as the side chain of 4-fluoroleucine, cyclohexylalanine and most preferably leucine. A representative compound of this embodiment has the formula:

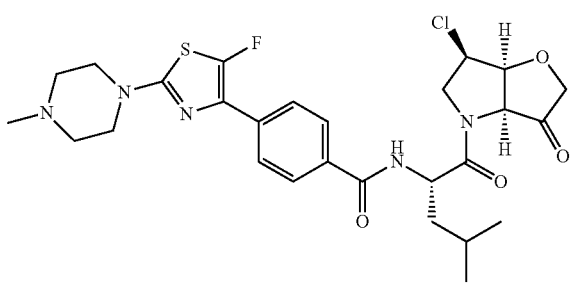 [SMILES: CC(C)C[C@H](NC(=O)c1ccc(-c2nc(N3CCN(C)CC3)sc2F)cc1)C(=O)N1C[C@@H](Cl)[C@H]2OCC(=O)[C@H]21]

Preferred embodiments of the invention include those denoted below, in each case with the stereochemistry depicted above in formula II:

N-[1-(6-chloro-3-oxo-hexahydro-furo[3,2-b]pyrrol-4-carbonyl)-3-methyl-butyl]-4-[2-(4-methyl-piperazin-1-yl)-thiazol-4-yl]-benzamide;

N-[2-(6-chloro-3-oxo-hexahydro-furo[3,2-b]pyrrol-4-yl)-1-cyclohexyl-2-oxo-ethyl]-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methyl-butyl]-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-propyl]-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-2-methyl-propyl]-4-[2-(4-methyl-piperazin-1-yl)-thiazol-4-yl]-benzamide;

N-[1-(6-chloro-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide;

N-[2-(6-choro-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;

N-[1-(6-chloro-3-oxo-hexahydro-furo[3,2-b]pyrrol-4-carbonyl)-2-methyl-butyl]-4-[5-methyl-2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-propyl]-4-[5-methyl-2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-2-methyl-propyl]-4-[5-methyl-2-(4-methyl-piperazin-1-yl)-thiazol-4-yl]-benzamide;

N-[1-(6-chloro-3-oxo-hexahydro-furo[3,2-b]pyrrol-4-carbonyl)-3-methyl-butyl]-4-[5-fluoro-2-(4-methyl-piperazin-1-yl)-thiazol-4-yl]-benzamide; N-[2-(6-choro-3-oxo-hexahydro-furo[3,2-b]pyrrol-4-yl)-1-cyclohexyl-2-oxo-ethyl]-4-[5-fluoro-2-(4-methyl-piperazin-1-yl)-thiazol-4-yl]-benzamide;

N-[1-(6-chloro-3-oxo-hexahydro-furo[3,2-b]pyrrol-4-carbonyl)-2-methyl-butyl]-4-[5-fluoro-2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-propyl]-4-[5-fluoro-2-(4-methyl-piperazin-1-yl)-thiazol-4-yl]-benzamide N-[1-(6-chloro-3-oxo-hexahydro-furo[3,2-b]pyrrol-4-carbonyl)-2-methoxy-2-methyl-propyl]-4-[5-fluorol-2-(4-methyl-piperazin-1-yl)-thiazol-4-yl]-benzamide;

N-[1-(6-chloro-3-oxo-hexahydro-furo[3,2-b]pyrrol-4-carbonyl)-3-methyl-butyl]-3-methyl-4-[2-(4-methyl-piperazin-1-yl)-thiazol-4-yl]-benzamide;

N-[2-(6-chloro-3-oxo-hexahydro-furo[3,2-b]pyrrol-4-yl)-1-cyclohexyl-2-oxo-ethyl]-3-methyl-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methyl-butyl]-3-methyl-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-propyl]-3-methyl-4-[2-(4-methyl-piperazin-1-yl)-thiazol-4-yl]-benzamide;

N-[1-(6-chloro-3-oxo-hexahydro-furo[3,2-b]pyrrol-4-carbonyl)-2-methoxy-2-methyl-propyl]-3-methyl-4-[2-(4-methyl-piperazin-1-yl)-thiazol-4-yl]-benzamide;
N-[1-(6-chloro-3-oxo-hexahydro-furo[3,2-b]pyrrol-4-carbonyl)-3-methyl-butyl]-3-methyl-4-[5-methyl-2-(4-methyl-piperazin-1-yl)-thiazol-4-yl]-benzamide;
N-[2-(6-choro-3-oxo-hexahydro-furo[3,2-b]pyrrol-4-yl)-1-cyclohexyl-2-oxo-ethyl]-3-methyl-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methyl-butyl]-3-methyl-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-propyl]-3-methyl-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-2-methyl-propyl]-3-methyl-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-3-methyl-butyl]-3-methyl-4-[5-fluoro-2-(4-methyl-piperazin-1-yl)-thiazol-4-yl]-benzamide;
N-[2-(6-choro-3-oxo-hexahydro-furo[3,2-b]pyrrol-4-yl)-1-cyclohexyl-2-oxo-ethyl]-3-methyl-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methyl-butyl]-3-methyl-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-propyl]-3-methyl-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-2-methyl-propyl]-3-methyl-4-[5-fluorol-2-(4-methyl-piperazin-1-yl)-thiazol-4-yl]-benzamide;
N-[1-(6-chloro-3-oxo-hexahydro-furo[3,2-b]pyrrol-4-carbonyl)-3-methyl-butyl]-3-fluoro-4-[2-(4-methyl-piperazin-1-yl)-thiazol-4-yl]-benzamide;
N-[2-(6-chloro-3-oxo-hexahydro-furo[3,2-b]pyrrol-4-yl)-1-cyclohexyl-2-oxo-ethyl]-3-fluoro-4-[2-(4-methyl-piperazin-1-yl)-thiazol-4-yl]-benzamide;
N-[1-(6-chloro-3-oxo-hexahydro-furo[3,2-b]pyrrol-4-carbonyl)-2-methyl-butyl]-3-fluoro-4-[2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-propyl]-3-fluoro-4-[2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-2-methyl-propyl]-3-fluoro-4-[2-(4-methyl-piperazin-1-yl)-thiazol-4-yl]-benzamide;
N-[1-(6-chloro-3-oxo-hexahydro-furo[3,2-b]pyrrol-4-carbonyl)-3-methyl-butyl]-3-fluoro-4-[5-methyl-2-(4-methyl-piperazin-1-yl)-thiazol-4-yl]-benzamide;
N-[2-(6-choro-3-oxo-hexahydro-furo[3,2-b]pyrrol-4-yl)-1-cyclohexyl-2-oxo-ethyl]-3-fluoro-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methyl-butyl]-3-fluoro-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-propyl]-3-fluoro-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-2-methyl-propyl]-3-fluoro-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-3-methyl-butyl]-3-fluoro-4-[5-fluoro-2-(4-methyl-piperazin-1-yl)-thiazol-4-yl]-benzamide;
N-[2-(6-choro-3-oxo-hexahydro-furo[3,2-b]pyrrol-4-yl)-1-cyclohexyl-2-oxo-ethyl]-3-fluoro-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methyl-butyl]-3-fluoro-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-propyl]-3-fluoro-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-2-methoxy-2-methyl-propyl]-3-fluoro-4-[5-fluorol-2-(4-methyl-piperazin-1-yl)-thiazol-4-yl]-benzamide;
and pharmaceutically acceptable salts, N-oxides and hydrates thereof.

Further preferred embodiments, with the stereochemistry depicted above include:
N-[1-(6-chloro-3-oxo-hexahydro-furo[3,2-b]pyrrol-4-carbonyl)-3-fluoro-3-methyl-butyl]-4-[2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-4-[5.methyl-2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-4-[5-fluoro-2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-3-methyl-4-[2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-3-fluoro-4-[2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-3-methyl-4-[5.methyl-2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-3-methyl-4-[5.fluoro-2-(4-methyl-piperazin-1-yl)-thiazol-4-yl]-benzamide
N-[1-(6-chloro-3-oxo-hexahydro-furo[3,2-b]pyrrol-4-carbonyl)-3-fluoro-3-methyl-butyl]-3-fluoro-4-[5-methyl-2-(4-methyl-piperazin-1-yl)-thiazol-4-yl]-benzamide;
N-[1-(6-chloro-3-oxo-hexahydro-furo[3,2-b]pyrrol-4-carbonyl)-3-fluoro-3-methyl-butyl]-3-fluoro-4-[5-fluoro-2-(4-methyl-piperazin-1-yl)-thiazol-4-yl]-benzamide;
and pharmaceutically acceptable salts, hydrates and N-oxides thereof.

Preferred embodiments of the invention include the compounds of formula II denoted:
N-[1-6-chloro-3-oxo-hexahydro-furo[3,2-b]pyrrole-4-carbonyl)-3-fluoro-3-methyl-butyl]-4-[2-(4-methyl-piperazin-1-yl)-thiazol-4-yl]benzamide;
N-[2-(6-Chloro-3-oxo-hexahydro-furo[3,2-b]pyrrole-4-yl)-1-cyclohexyl-2-oxo-ethyl]-4-[2-(4-methyl-piperazin-1-yl)-thiazol-4-yl]-benzamide
N-[1-(6-chloro-3-oxo-hexahydro-furo[3,2-b]pyrrole-4-carbonyl)-3-methyl-butyl]-4-[2-(4-methyl-piperazin-1-yl)-thiazol-4-yl]benzamide
N-[1-(6-chloro-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide; or
a pharmaceutically acceptable salt, hydrate or N-oxide thereof.

Particularly preferred embodiments of the invention include the compound of formula II denoted N-[1-(6-Chloro- 3-oxo-hexahydro-furo[3,2-b]pyrrole-4-carbonyl)-3-methyl-butyl]-3-fluoro-4-[2-(4-methyl-piperazin-1-yl)-thiazol-4-yl]-benzamide; or
a pharmaceutically acceptable salt, hydrate or N-oxide thereof.

Particularly preferred embodiments of the invention include the compound of formula II denoted N-[1-(6-Chloro-3-oxo-hexahydro-furo[3,2-b]pyrrole-4-carbonyl)-3-methyl-butyl]-4-[5-fluoro-2-(4-methyl-piperazin-1-yl)-thiazol-4-yl]-benzamide; or
a pharmaceutically acceptable salt, hydrate or N-oxide thereof.

Additional aspects of the invention include a pharmaceutical composition comprising a compound as defined above and a pharmaceutically acceptable carrier or diluent therefor.

A further aspect of the invention is the use of a compound as defined above for the treatment of, or in the manufacture of a medicament for the treatment of, disorders mediated by cathepsin K, such as:
osteoporosis,
gingival diseases such as gingivitis and periodontitis,
Paget's disease,
hypercalcaemia of malignancy
metabolic bone disease
diseases characterised by excessive cartilage or matrix degradation, such as osteoarthritis and rheumatoid arthritis,
bone cancers including neoplasia,
pain, especially chronic pain.

Also provided is a method for the treatment or prevention of a disorder mediated by cathepsin K, comprising the administration of a safe and effective amount of a compound according to the claims to a subject in need thereof. Such subjects will typically be mammals, in particular humans.

The compounds of the invention can form salts which form an additional aspect of the invention. Appropriate pharmaceutically acceptable salts of the compounds of Formula II include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

The compounds of the invention may in some cases be isolated as the hydrate. Hydrates are typically prepared by recrystallisation from an aqueous/organic solvent mixture using organic solvents such as dioxin, tetrahydrofuran or methanol. Hydrates can also be generated in situ by administration of the corresponding ketone to a patient.

The N-oxides of compounds of the invention can be prepared by methods known to those of ordinary skill in the art. For example, N-oxides can be prepared by treating an unoxidized form of the compound of the invention with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of the invention can be prepared from the N-oxide of an appropriate starting material.

Examples of N-oxides of the invention include those with the partial structures:

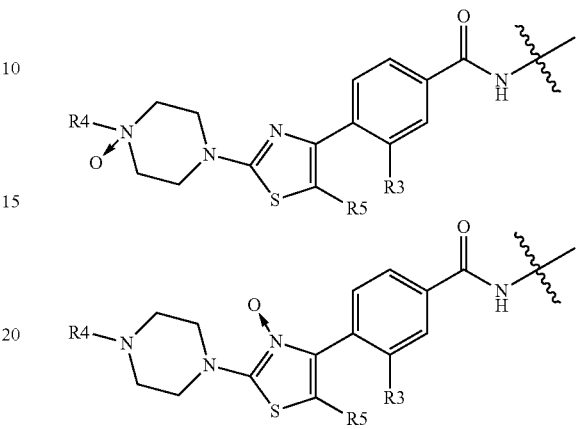

Compounds of the invention in unoxidized form can be prepared from N-oxides of the corresponding compounds of the invention by treating with a reducing agent (e.g., sulfur, sulfur dioxide, triphenyl phosphine, lithium borohydride, sodium borohydride, phosphorus bichloride, tribromide, or the like) in an suitable inert organic solvent (e.g., acetonitrile, ethanol, aqueous dioxane, or the like) at 0 to 80° C.

It should be noted that the radical positions on any molecular moiety used in the definitions may be anywhere on such moiety as long as it is chemically stable.

Radicals used in the definitions of the variables include all possible isomers unless otherwise indicated.

When any variable occurs more than one time in any constituent, each definition is independent.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Compounds of the invention can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline; diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography, for example HPLC or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

It will be appreciated that the invention extends to prodrugs, solvates, complexes and other forms releasing a compound of the invention in vivo.

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula II or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The appropriate dosage for the compounds or formulations of the invention will depend upon the indication and the patient and is readily determined by conventional animal trials and confirmed with human clinical trials. Dosages providing intracellular (for inhibition of physiological proteases of the papain superamily) concentrations of the order 0.01-100 µM, more preferably 0.01-10 µM, such as 0.1-25 µM are typically desirable and achievable.

Compounds of the invention are prepared by a variety of solution and solid phase chemistries.

The compounds are typically prepared as building blocks reflecting the P1, P2 and P3 moieties of the end product inhibitor. Without in any way wishing to be bound by theory, or the ascription of tentative binding modes for specific variables, the notional concepts P1, P2 and P3 as used herein are provided for convenience only and have substantially their conventional Schlecter & Berger meanings and denote those portions of the inhibitor believed to fill the S1, S2, and S3 subsites respectively of the enzyme, where S1 is adjacent the cleavage site and S3 remote from the cleavage site. Compounds defined by Formula II are intended to be within the scope of the invention, regardless of binding mode.

Broadly speaking the P1 building block will have the formula:

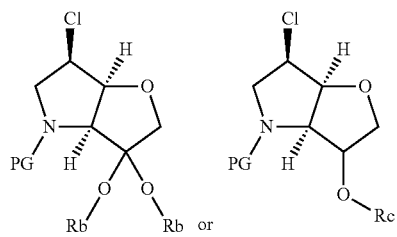

wherein

PG is a conventional N-protecting group or the free amine;

the two Rb groups define a ketal, such as the bis methyl ketal or together define a cyclic ketal such as 1,3-dioxolane;

and Rc is an hydroxy protecting group, or less commonly is H or represents the keto function of the end-product inhibitor in cases where the P1 building block as the ketone is elongated with P2 and P3.

P2 is typically an N-protected L-leucine, L-isoleucine, O-methyl-L-threonine, L-3-hydroxyvaline, 4-fluoroleucine or L-cyclohexylglycine, and P3 typically comprises a capping group such as a benzoic acid derivative with the N-alkylpiperazinyl-E moiety already introduced or provided with a synthon therefor in the para position.

The suitably protected individual building blocks can first be prepared and subsequently coupled together, preferably in the sequence P2+P1→P2–P1 followed by N-alkylpiperazinyl-thiazolyl-benzoic acid*+P2–P1→N-alkylpiperazinyl-thiazolyl-benzoate-P2–P2–P1, where * denotes an activated form, in order to minimise racemisation at P2.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent non-natural amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

The alpha-carboxyl group of the C-terminal residue is usually protected as an ester that can be cleaved to give the carboxylic acid. Protecting groups that can be used include 1) alkyl esters such as methyl, trimethylsilyl and tert-butyl, 2) aralkyl esters such as benzyl and substituted benzyl, or 3) esters that can be cleaved by mild base or mild reductive means such as trichloroethyl and phenacyl esters.

The alpha-amino group of each amino acid to be coupled is typically N-protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxy-carbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred alpha-amino protecting group is either Boc or Fmoc. Many amino acid derivatives suitably protected for peptide synthesis are commercially available.

The alpha-amino protecting group is typically cleaved prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Once the inhibitor sequence is completed any remaining protecting groups are removed in whatever manner is dictated by the choice of protecting groups. These procedures are well known to those skilled in the art.

The first stage in a synthesis of compounds of the invention, such as those of the general formula II is typically the preparation in solution of a functionalized P1 building block, for example as shown in the scheme below:

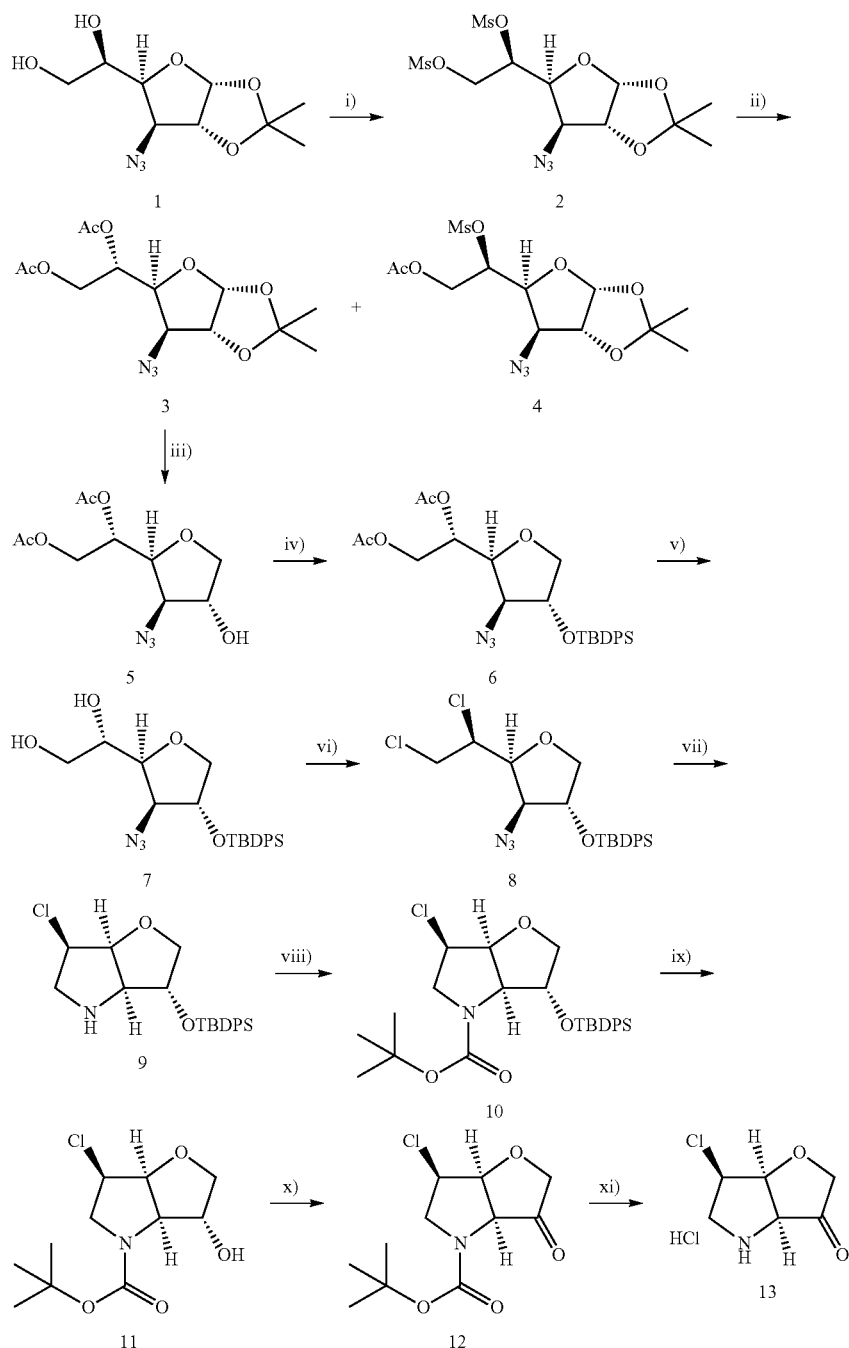

i) MsCl, Pyr ii) NaOAc, Ac₂O, DMF, 130 C iii) BF₃xEt₂O, Et₂SiH, DCM iv) TBDPS-Cl, Im-H, DMF v) NaOMe vi) SO₂Cl₂, Pyr, DCM vii) PPh₃, MeOH, H₂O, then Et₃N, 50 C viii) Boc₂O, Et₃N ix) TBAF, THF x) Dess-Martin Periodinane xi) method a: MeOH, TMOF, p-TsOH, then Et₃N, Boc₂O, then chromatography and finally MeOH, AcCl, method b: MeOH, AcCl, TMOF Although the scheme above has been illustrated with a differential protecting group strategy employing acetyl, mesyl, TBDPS and Boc, it will be apparent that other permutations of conventional protecting groups, as described by Greene (ibid) can be employed. Additionally, it may be convenient to employ the dimethyl hemiacetal of the ketone group during coupling of P2 and P3 residues and to regenerate the ketone function in a latter step.

Elongation of the building block with the P2 and P3 building blocks is typically carried out in the presence of a suitable coupling agent e.g., benzotriazole-1-yloxytrispyrrolidino-phosphonium hexafluorophosphate (PyBOP), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl carbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N dimethylformamide, ethereal solvents such as tetrahydrofuran, dioxane, and the like.

Alternatively, the above elongation coupling step can be carried out by first converting the P3/P2 building block into an active acid derivative such as succinimide ester and then reacting it with the P1 amine. The reaction typically requires 2 to 3 h to complete. The conditions utilized in this reaction depend on the nature of the active acid derivative. For example, if it is an acid chloride derivative, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

P2 building blocks in the form of N-protected L-amino acids are readily available commercially, for example L-leucine, L-isoleucine, L-cyclohexylglycine, O-methyl-L threonine and others are available commercially with a number of protecting group variants such as CBz, Boc or Fmoc. Other variants of $R^2$ are easily prepared from commercially available start materials. For example compounds wherein $R^2$ is $—C(CH_3)_2OCH_3$ can be prepared by reacting CBz protected (S)-(+)-2-amino-3-hydroxy-3-methylbutanoic acid with 3,3-dimethoxy-hexahydro-furo(3,2b)pyrrole to form the desired P2–P1 unit. The P2 side chain alcohol can now be methylated using methyliodide under conventional sodium hydride, imidazole, THF conditions to obtain the desired P2 without substantial racemisation of the alpha centre. This P2–P1 moiety can now be carried through the synthesis as described herein, namely CBz removal and coupling.

WO05/565299 describes the preparation of a gamma-fluoroleucine P2 building block. An alternative synthesis of Fmoc and N-Boc-gammafluoroleucine building blocks is shown in Truong et al SynLett 2005 no 8 1278-1280.

The preparation of P3 building blocks is described in WO05/66180 or readily prepared by analogous methods. For example, the scheme below shows the preparation of a fluoro-substituted thiazolyl:

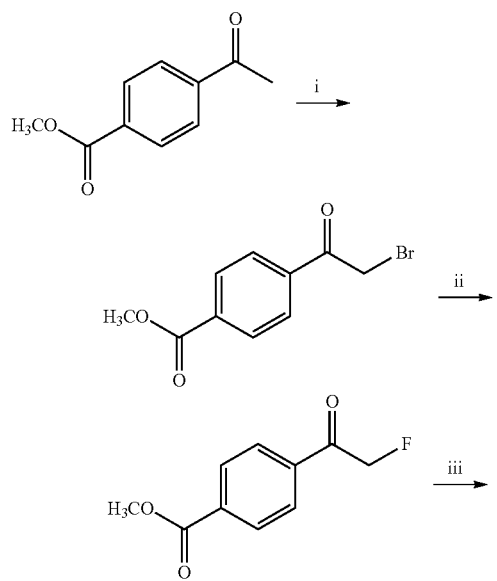

-continued

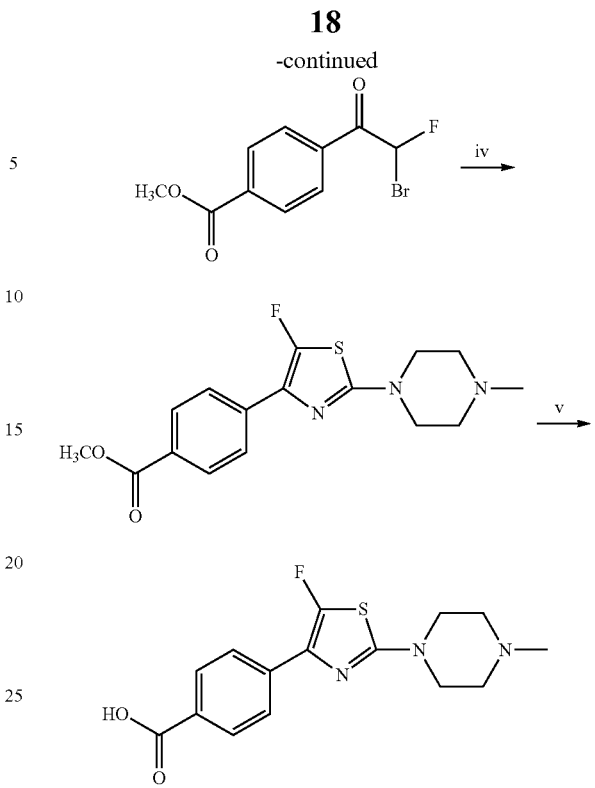

i. HOAc, Br$_2$, RT, 2 h, 55% yield; ii. KF, 18-crown-6, CH$_3$CN, 90° C., 16 h, 31% yield; iii. HOAc, Br$_2$, 45° C., 4 h, 100% yield; iv. 4-methyl-piperazine-1-carbothioamide, ethanol, 70° C., 2 h, 74% yield, v. LiOH, THF, H$_2$O, RT, 16 h, 79% yield.

Synthesis of 4-[5-fluoro-2-(4-methyl-piperazin-1-yl)-thiazol-4-yl]-benzoic acid

The starting material, methyl 4-acetylbenzoate, is commercially available. Bromination at the α-position to the ketone is achieved with bromine in acetic acid to provide the desired 4-(2-bromo-acetyl)-benzoic acid methyl ester. Subsequent treatment of 4-(2-bromo-acetyl)-benzoic acid methyl ester with potassium fluoride in the presence of 18-crown-6 at 90° C., provides 4-(2-fluoro-acetyl)-benzoic acid methyl ester after column chromatography. Repeated bromination at the α-position to the ketone is achieved with bromine in acetic acid to provide the desired 4-(2-bromo-2-fluoro-acetyl)-benzoic acid methyl ester. Formation of the thiazole is typically carried out by heating 4-(2-bromo-2-fluoro-acetyl)-benzoic acid methyl ester with 4-methylpiperazine-1-carbothioamide at 70° C. for 2 hours. On cooling, the desired 4-[5-fluoro-2-(4-methyl-piperazin-1-yl)-thiazol-4-yl]-benzoic acid methyl ester precipitates out. Deprotection of the methyl ester is carried out using a lithium hydroxide solution and the desired acid, 4-[5-fluoro-2-(4-methyl-piperazin-1-yl)-thiazol-4-yl]-benzoic acid is generally obtained in good yield as the dihydrochloride salt on workup with hydrochloric acid.

WO05/066159 and WO05/065578 describe the preparation of compounds wherein the P2 and P3 units are linked together via a C(CF$_3$) moiety including those wherein P3 is a biphenylsulphone. An example of the preparation of such a P2–P3 building block suitable for the preparation for compounds of formula II wherein Rq is trifluoromethyl and Rq' is H is shown in scheme 3.

Scheme 3

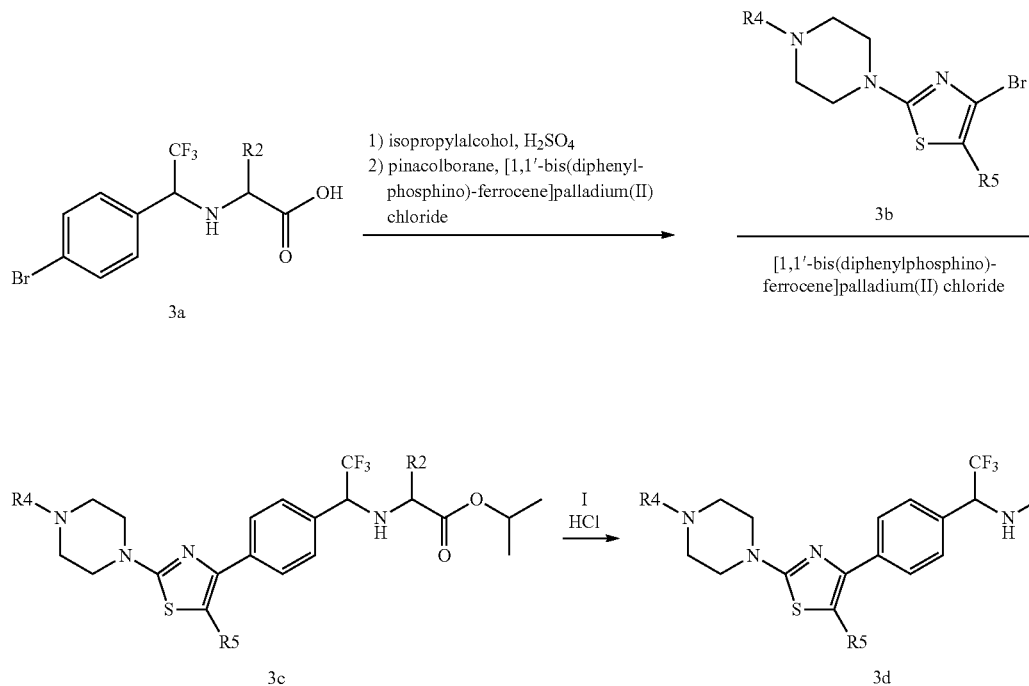

Protection of the acid function of the bromo derivative (3a), prepared according to the procedure described in Bioorg. Med. Chem Lett. 2006, 16, 1985, by reaction with for instance isopropylalcohol in the presence of an acid such as sulphuric acid, provides the corresponding ester. A desired thiazole derivative can then be coupled to the aromatic group of the afforded ester using for example Stille or Suzuki coupling conditions. For example, the ester of the bromo derivative 3a can be reacted with a borane reagent like pinacolborane in the presence of [1,1'-bis(diphenylphosphino)-ferrocene]palladium II chloride to provide the corresponding dioxoborolane derivative. Subsequent substitution of the boronic group by a desired thiazole derivative (3b) in the presence of [1,1'-bis(diphenylphosphino)-ferrocene]palladium II chloride then gives the biaryl derivative (3c). Thiazole derivatives (3b) can be prepared for example as described in J. Med. Chem. 2005, 48, 7520-7534. Removal of the acid protection group for example by treatment with an acid such as hydrochloride acid in dioxane provides the P2–P3 building block ready for coupling to a P1 building block to provide compounds of the invention. WO07/006716 shows the preparation and coupling of such P3 and P3–P2 building blocks.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

DETAILED DESCRIPTION OF THE EMBODIMENTS

Various embodiments of the invention will now be described by way of illustration only with reference to the following Examples.

EXAMPLE 1

Preparation of P1 Building Block

Step a)

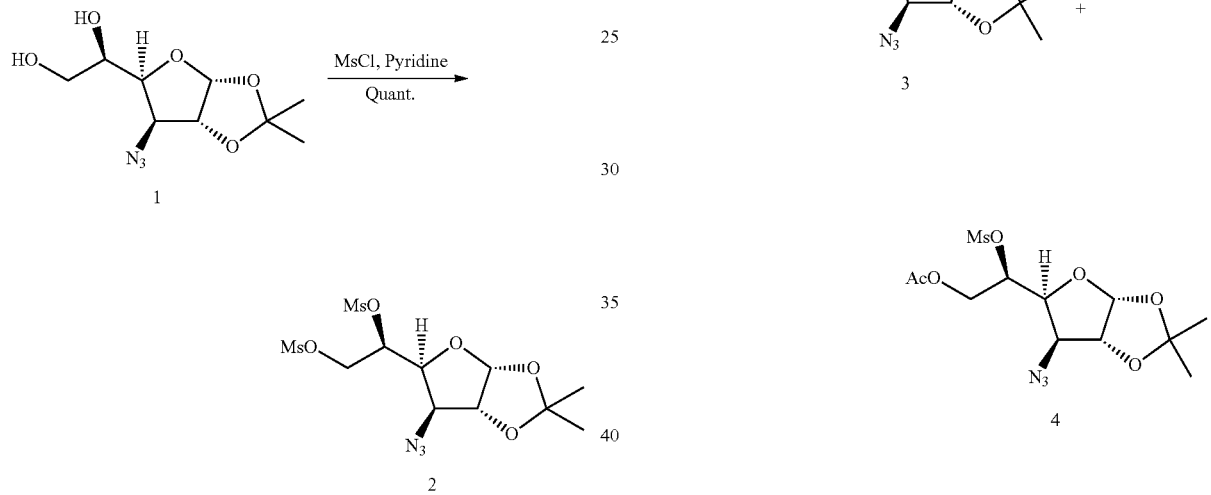

Step b)

1 (7.0 g, 28.5 mmol) (3-azido-3-deoxy-1,2-O-(1-methylethylidene)-α-D-allofuranose prepared as described in Tronchet, Jean M. J.; Gentile, Bernard; Ojha-Poncet, Joelle; Moret, Gilles; Schwarzenbach, Dominique; Barbalat-Rey, Francoise; Tronchet, Jeannine. Carbohydrate Research (1977), 59(1), 87-93) was dissolved in dry pyridine (50 mL) and the solution cooled to 0° C. Mesyl chloride was slowly added to the solution and the solution allowed to warm up to room temperature. The reaction was stirred overnight and after 14 hrs MeOH (10 mL) was added followed by EtOAc (150 mL). The solution was washed three times with 2 M H$_2$SO$_{4\ (aq)}$ (3×100 mL) and two times with NaHCO$_3$ sat.$_{(aq)}$ (2×100 mL) and thereafter the organic phase was dried with Na$_2$SO$_4$, filtered and concentrated in vacuo. After the product was put on a high vacuum pump overnight to remove residual solvents, product 2 was obtained as a pale yellow oil in quantitative yield (11.5 g).

$^1$H NMR (CDCl$_3$, 400 MHz) 1.34 (s, 3H), 1.51 (s, 3H), 3.07 (s, 3H), 3.16 (s, 3H), 4.18 (d, 1H, J=3.1), 4.36 (dd, 1 H, J=8.6, 3.2), 4.42 (dd, 1H, J=12.0, 5.0), 4.67 (dd, 1H, J=11.9, 2.3), 4.74 (d, 1H, J=3.7), 5.11 (ddd, 1H, J=8.6, 5.0, 2.3), 5.89 (d, 1H, J=3.6).

Compound 2 (11.5 g, 28.5 mmol) was dissolved in DMF (50 mL). NaOAc (23.4 g, 285 mmol) and Ac$_2$O (48.6 mL, 0.514 mol) was added to the solution, which was then heated to 125° C. for 86 hrs. Some of the solvent was removed by rotary evaporation before addition of 500 mL EtOAc. The very dark solution was filtered through Celite. The organic phase was then washed with H$_2$O (3×350 mL). The organic phase was dried with Na$_2$SO$_4$, filtered and the solvent was removed by rotary evaporation. The crude products were purified by flash column chromatography (heptane:ethyl acetate 7:3->2:1) giving desired compound 3 in 61% yield (5.70 g) and compound 4 in 22% yield (2.34 g).

Compound 3: $^1$H NMR (CDCl$_3$, 400 MHz) 1.34 (s, 3H), 1.53 (s, 3H), 2.09 (s, 3H), 2.11 (s, 3H), 3.94 (d, 1H, J=3.4), 4.19 (dd, 1H, J=12.2, 5.0), 4.32 (dd, 1H, J=8.0, 3.3), 4.37 (dd, 1H, J=12.3, 3.5), 4.73 (d, 1H, J=3.6), 5.32-5.37 (m, 1H), 5.94 (d, 1H, J=3.8).

Compound 4: $^1$H NMR (CDCl$_3$, 400 MHz) 1.34 (s, 3H), 1.51 (s, 3H), 2.10 (s, 3H), 3.10 (s, 3H), 4.11 (d, 1H, J=3.6), 4.21 (dd, 1H, J=12.8, 6.2), 4.32 (dd, 1H, J=8.3, 3.2), 4.65 (dd, 1H, J=12.7, 2.2), 4.73 (d, 1H, J=3.5), 5.09 (ddd, 1H, J=8.3, 6.1, 2.3), 5.89 (d, 1H, J=3.5).

Step c)

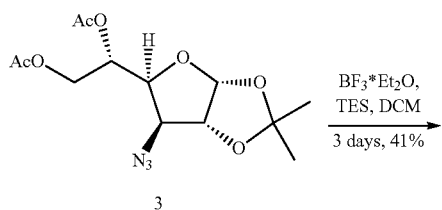

Triethyl silane (27.6 mL, 173 mmol) was added to compound 3 (5.70 g, 17.3 mmol) dissolved in dry DCM (40 mL). The round bottomed flask was placed under an inert atmosphere (N$_2$) in an ice bath, and allowed to cool, before slow addition of BF$_3$.Et$_2$O (23.1 mL, 173 mmol). The reaction proceeded slowly and was stirred for 3 days. After this time, starting material was still present. Slow addition of NaHCO$_3$ $_{(sat, aq)}$ (70 mL) was followed by spoonwise addition of solid NaHCO$_3$ until the gas evolution ceased. The aqueous phase was extracted with DCM (150 mL) and washed with NaHCO$_3$ $_{(sat, aq)}$ (70 mL) abd subsequently NH$_4$Cl$_{(sat, aq)}$ (70 mL). The organic phase was dried with Na$_2$SO$_4$, filtered and concentrated in vacuo. The crude product was purified by flash column chromatography (Heptane:Ethyl acetate (2:1) to give a yield of 41% (1.95 g) of compound 5. 0.69 g of unchanged starting material was also isolated.

$^1$H NMR (CDCl$_3$, 400 MHz) 2.08 (s, 3H), 2.11 (s, 3H), 3.72 (dd, 1H, J=10.0, 2.6), 3.95 (dd, 1H, J=4.6, 2.1), 4.17-4.27 (m, 3H), 4.37 (dd, 1H, J=12.1, 3.7), 4.52-4.57 (m, 1H), 5.26-5.31 (m, 1H).

Step d)

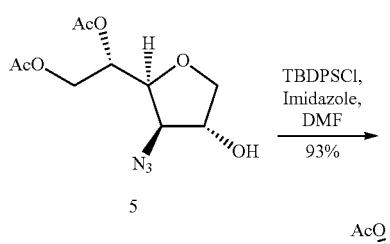

Imidazole (1.46 g, 21.4 mmol) was added to a solution of compound 5 (1.95 g, 7.14 mmol) in DMF (50 mL). TBDPSCl was added after a couple of minutes and the reaction was stirred at room temperature overnight. Ethyl acetate (200 mL) was added to the reaction and the solution was washed with 10% citric acid$_{(aq)}$ (3×50 mL) and NaHCO$_3$ $_{(sat, aq)}$ (50 mL). The organic phase was dried with Na$_2$SO$_4$, filtered and concentrated in vacuo. The crude product was purified by flash column chromatography (Heptane:Ethyl acetate (4:1) to give 6 in a yield of 92% (3.39 g).

$^1$H NMR (CDCl$_3$, 400 MHz) 1.09 (s, 9H), 2.04 (s, 3H), 2.05 (s, 3H), 3.71 (dd, 1H, J=4.3, 2.1), 3.78 (dd, 1H, J=9.5, 2.2), 3.99 (dd, 1H, J=9.6, 4.6), 4.12 (dd, 1H, J=12.2, 5.1), 4.28-4.33 (m, 2H), 4.36-4.40 (m, 1H), 5.17-5.22 (m, 1H), 7.37-7.51 (m, 6H), 7.58-7.74 (m, 4H).

Step e)

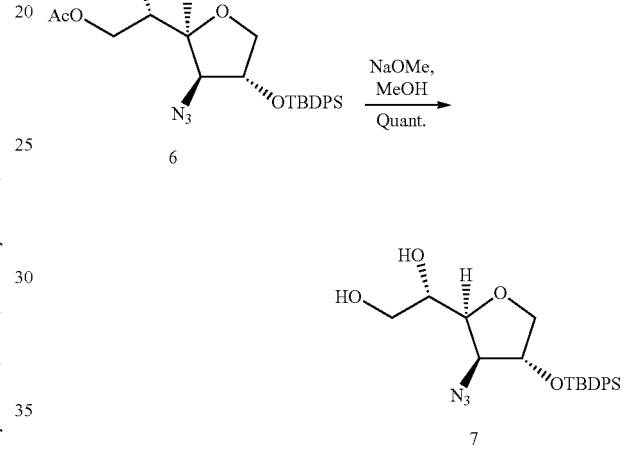

NaOMe (10 mL, 0.5 M in MeOH) was added to a solution of 6 (3.39 g, 6.63 mmol) dissolved in MeOH (60 mL). The reaction was stirred at room temperature for 2 hrs before the solution was neutralized by adding Dowex 50 WX8 (H$^+$ form) until a neutral pH was reached. The beads were filtered off and the solvent was removed by rotary evaporation followed by high vacuum. The product 7 was obtained in quantitative yield (2.66 g).

$^1$H NMR (CDCl$_3$, 400 MHz) 1.08 (s, 9H), 3.64 (dd, 1H, J=11.5, 5.5), 3.71 (dd, 1H, J=11.4, 3.9), 3.73-3.77 (m, 2H), 3.85-3.90 (m, 1H), 3.95 (dd, 1H, J=9.6, 4.7), 4.15 (dd, 1H, J=6.1, 4.2), 4.39-4.43 (m, 1H), 7.37-7.51 (m, 6H), 7.58-7.74 (m, 4H).

Step f)

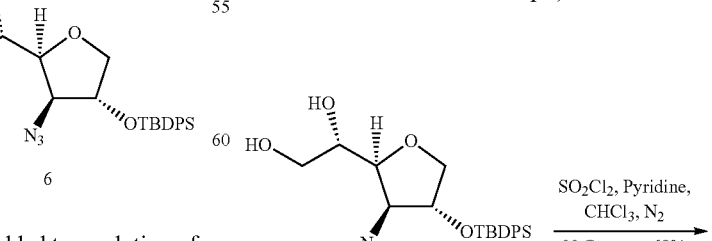

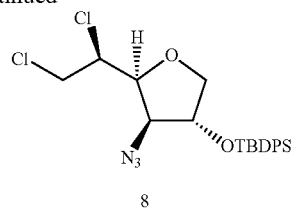

8

Compound 7 (1.4 g, 3.27 mmol), dissolved in chloroform (10 mL) and pyridine (4.77 mL, 58.9 mmol) was cooled in a dry ice, acetone bath. SO₂Cl₂ (1.56 mL, 19.6 mmol) was added and the bath was thereafter removed. The reaction mixture was stirred overnight and became darker over time. After 16 hrs the reaction mixture was diluted with DCM (15 mL) and washed with 10% citric acid (aq) (15 mL) and NaHCO₃ (sat, aq) (15 mL). The organic phase was dried with Na₂SO₄, filtered and concentrated in vacuo. The brown oil was dissolved in MeOH (10 mL) and approx. 0.5 mL of NaI (0.8% in MeOH:H₂O (1:1)) was added to the solution that was stirred for 15 minutes. The solvent was then evaporated and the crude product was purified by flash column chromatography (Heptane:Ethyl acetate (4:1) to give a yield of 68% of compound 8.

¹H NMR (CDCl₃, 400 MHz) 1.10 (s, 9H), 3.80-3.85 (m, 2H), 3.89 (dd, 1H, J=12.1, 5.8), 3.96 (dd, 1H, J=9.7, 3.8), 4.00 (dd, 1H, J=12.3, 2.6), 4.15 (ddd, 1H, J=9.7, 5.9, 2.6), 4.32-4.36 (m, 2H), 7.35-7.52 (m, 6H), 7.58-7.75 (m, 4H)

Step g)

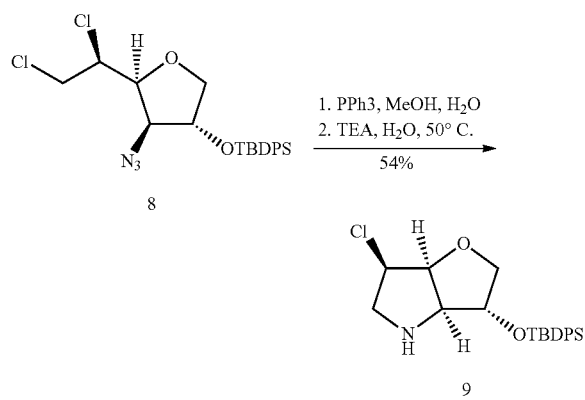

PPh₃ (882 mg, 3.36 mmol) was added to a solution of compound 8 (1.04 g, 2.24 mmol) dissolved in MeOH (50 mL) and H₂O (5 mL). The reaction was stirred at room temperature over night. LC-MS showed no starting material but very little cyclized product. TEA (9.38 mL, 67.2 mmol) and H₂O (5 mL) was added to the solution which was heated to 50° C. After 4 hrs LC-MS showed no non-cyclized amine. The solvent was evaporated and the crude product purified by flash chromatography (heptane:ethyl acetate (3:2)) to give product 9 in 54% yield (0.49 g). LRMS (M+H) 402.

¹H NMR (CDCl₃, 400 MHz) 1.06 (s, 9H), 2.71 (dd, 1H, J=11.1, 10.4), 3.18 (dd, 1H, J=11.2, 7.0), 3.73 (d, 1H, J=4.7), 3.78 (dd, 1H, J=9.8, 3.5), 3.84 (dd, 1H, J=9.8, 2.0), 3.95 (ddd, 1H, J=10.2, 7.1, 4.1), 4.16-4.19 (m, 1H), 4.66 (dd, 1H, J=4.4, 4.4), 7.35-7.46 (m, 6H), 7.61-7.67 (m, 4H).

Step h)

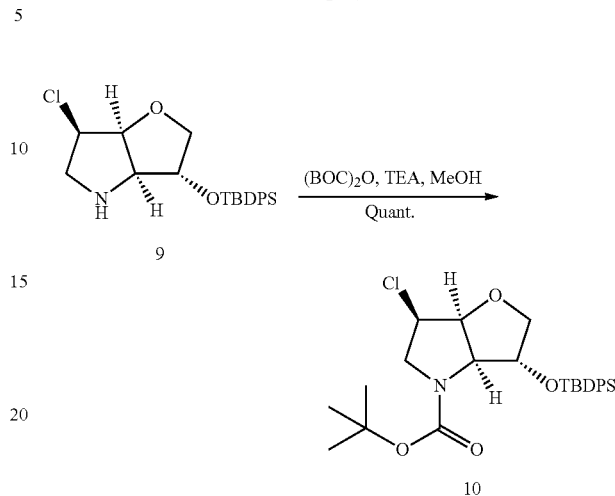

BOC anhydride (0.52 g, 2.40 mmol) was added to a solution of compound 9 (0.48 g, 1.20 mmol) dissolved in 50 mL of MeOH:TEA (9:1). The reaction was stirred overnight and thereafter the solvent was removed by concentration in vacuo. The crude product was purified by flash column chromatography (heptane:ethyl acetate (4:1->2:1)) to give the product 10 in quantitative yield (0.60 g).

¹H NMR (CDCl₃, 400 MHz) 1.07 (s, 9H), 1.24-1.46 (m, 9H)*, 3.05 (dd, 1H, J=10.4, 10.4), 3.56 (d, 1H, J=9.7), 3.70-3.89 (m, 1H)*, 3.90-4.15 (m, 2H)*, 4.24-4.89 (m, 3H)*, 7.34-7.47 (m, 6H), 7.59-7.78 (m, 4H). * Denotes rotamers.

Step i)

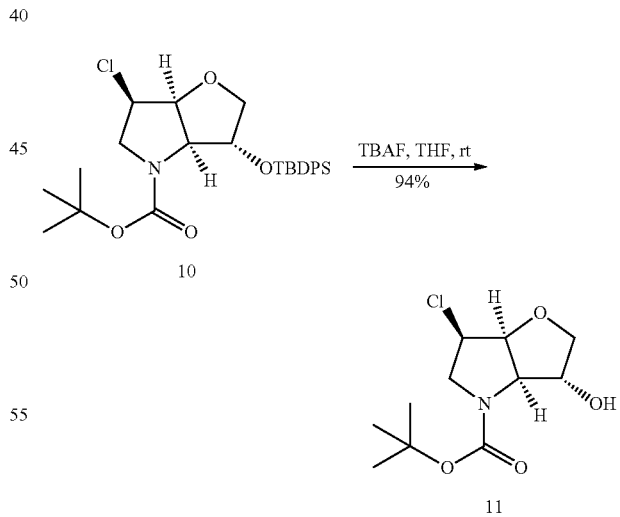

Tetrabutylammonium flouride (1.79 mL, 1.79 mmol) was added to a solution of compound 10 (0.60 g, 1.19 mmol) dissolved in THF (12 mL). The reaction was stirred at room temperature for 3 hrs before the solvent was removed by concentration in vacuo. The crude product was purified by flash column chromatography (hetane:ethyl acetate (1:1->0:1) and obtained in 94% yield (0.29 g) compound 11.

$^1$H NMR (CDCl$_3$, 400 MHz) 1.45-1.52 (m, 9H)*, 3.16-3.32 (m, 1H)*, 3.83-4.22 (m, 5H)*, 4.41-4.54 (m, 1H)*, 4.66-4.71 (m, 1H)*. * Denotes rotamers.

Step j)

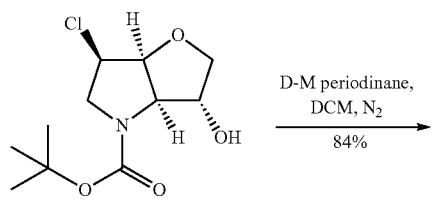

Dess-Martin periodinane (0.60 g, 1.42 mmol) was added to a solution of compound 11 (0.34 g, 1.29 mmol) dissolved in dry DCM. The reaction was stirred under N$_2$ for 2 hrs when the reaction was deemed to have reached completed by tlc. The solution was washed 3 times (3×20 mL) with a 1:1 mixture of 10% Na$_2$S$_2$O$_3$ $_{(aq)}$ and NaHCO$_3$ $_{(sat, aq)}$. The organic phase was dried with Na$_2$SO$_4$, filtered and concentrated in vacuo The crude product was purified by flash chromatography (Heptane:Ethyl acetate (3:1) to give a yield of 84% (284 mg) of compound 12.

$^1$H NMR (CDCl$_3$, 400 MHz) 1.48 (s, 9H), 3.45 (dd, 1H, J=11.3, 9.0), 4.01-4.17 (m, 2H), 4.19-4.41 (m, 3H), 4.68-4.87 (m, 1H).

Step k)

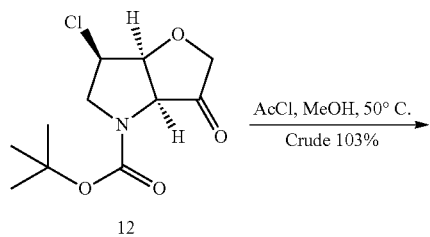

A pre-mixed solution of AcCl (42 μL, 0.601 mmol) and MeOH (5 mL) was added to a solution of compound 12 (263 mg, 1.01 mmol). After stiffing for 2 hrs, additional AcCl (0.98 mL, 14 mmol) was added and again after stiffing for 16 hrs, additional AcCl (9.8 mL, 140 mmol) was added. The reaction was completed shortly thereafter concentrated in vacuo and subsequently any residual solvent was removed by high vacuum to give 103% crude yield (253 mg) of compound 13.

$^1$H NMR (CDCl$_3$, 400 MHz) 3.34 (s, 3H), 3.40 (s, 3H), 3.76 (d, 1H, J=10.6), 3.72-3.90 (m, 1H), 4.15 (d, 1H, J=10.4), 4.34 (d, 1H, J=4.6), 4.50-4.60 (m, 1H), 4.69-4.75 (m, 1H), 4.83 (s, 1H).

EXAMPLE 2

P-2 Coupling with L-Leu

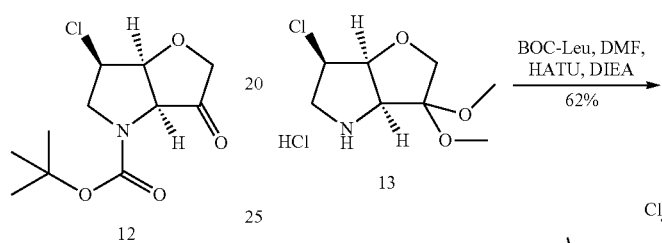

DIEA (304 μL, 1.84 mmol) and BOC-Leu (117 mg, 0.506 mmol) was added to crude 13 (112 mg, 0.460 mmol), dissolved in DMF (6 mL). The reaction flask was cooled in an ice bath for 10 minutes before addition of HATU (193 mg, 0.506 mmol). The reaction was stirred for 3 hours at room temperature before concentration in vacuo. The crude residue was dissolved in CHCl$_3$ (15 mL) and washed with 10% citric acid$_{(aq)}$ (10 mL) and NaHCO$_3$ $_{(sat, aq)}$ (10 mL). The organic phase was dried with Na$_2$SO$_4$, filtered and evaporated. The crude product was purified by flash chromatography (Heptane:Ethyl acetate (2:1->1:1) to give product 14 in a yield of 62% (121 mg).

EXAMPLE 3

P3 Building Block

4-[5-methyl-2-(4-methyl-piperazin-1-yl)-thiazol-4-yl]-benzoic acid

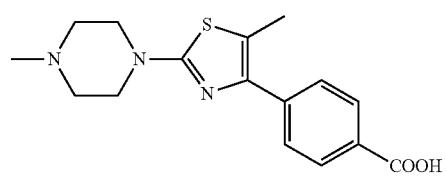 [SMILES: Cc1sc(N2CCN(C)CC2)nc1-c1ccc(C(=O)O)cc1]

Step a) 4-Cyanopropiophenone

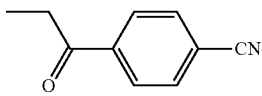

As described for the preparation of 4-cyanoacetophenone (Synth. Commun 1994, 887-890), a mixture of 4-bromopropiophenone (5.65 g, 26.4 mmol), Zn(CN)$_2$ (1.80 g, 15.3 mmol), and Pd(PPh$_3$)$_4$ (2.95 g, 2.6 mmol) was refluxed at 80° C. in deoxygenated DMF (35 mL, stored over 4 Å molecular sieves, bubbled with Ar before use) for 18 h. The mixture was partitioned between toluene (100 mL) and 2N NH$_4$OH (100 mL). The organic phase was extracted with 2N NH$_4$OH (100 mL), washed with saturated aqueous NaCl (2×100 mL), dried, and concentrated in vacuo. A 10 mmol scale reaction was done similarly and the crude products were combined. Flash chromatography (330 g silica, 6/1 petroleum ether-EtOAc) afforded the desired compound as a white solid (5.17 g, 89%).

$^1$H NMR (CDCl$_3$) δ ppm: 1.22 (t, 3H, J=7.2 Hz), 3.00 (q, 2H, J=7.3 Hz), 7.75 (d, 2H, J=8.8 Hz), 8.03 (d, 2H, J=8.4 Hz)

13C NMR (CDCl$_3$) δ ppm: 7.8, 32.1, 116.1, 117.9, 128.3, 132.4, 139.7, 199.2

Step b) 4-Propionylbenzoic acid

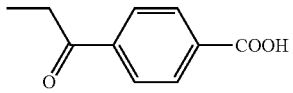

4-Cyanopropiophenone (4.67 g, 29.3 mmol) was refluxed with 2N NaOH (90 mL, 180 mmol) and dioxane (90 mL) at 95° C. overnight. The mixture was diluted with water (150 mL), washed with ether (75 mL), acidified to pH 2 with concentrated HCl, and extracted with ether (3×75 mL). The organic phase was washed with saturated aqueous NaCl (3×75 mL), dried, and concentrated to give a yellow solid (5.12 g, 98%).

1H NMR (CDCl$_3$+CD$_3$OD) δ ppm: 1.18 (t, 3H, J=7.2 Hz), 2.99, (q, 2H, J=7.1 Hz), 7.95 (d, 2H, J=8.4 Hz), 8.08 (d, 2H, J=8.8 Hz)

13C NMR (CDCl$_3$) δ ppm: 7.9, 32.1, 127.7, 130.0, 134.0, 140.0, 168.0, 200.8

Step c) Methyl 4-propionylbenzoate

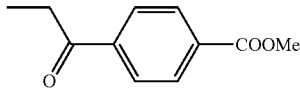

The benzoic acid above (890 mg, 5 mmol), NaHCO$_3$ (1.26 g, 15 mmol) and iodomethane (935 µL, 15 mmol) in DMF (10 mL) were stirred at RT overnight. The mixture was diluted with saturated aqueous NaCl (50 mL) and extracted with ether (3×50 mL). The organic phase was washed with water (50 mL), dried, and concentrated. Flash chromatography (90 g silica, 2/1 petroleum ether-EtOAc) gave a white solid (744 mg, 77%).

1H NMR (CDCl$_3$) δ ppm: 1.24 (t, 3H, J=7 Hz), 3.03 (q, 2H, J=7 Hz), 3.95 (s, 3H), 8.0 and 8.12 (ABq, 4H)

Step d) Methyl 4-(2-bromopropionyl)benzoate

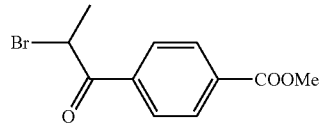

Methyl 4-propionylbenzoate (744 mg, 3.87 mmol), pyrrolidone hydrotribromide (1.98 g), and 2-pyrrolidinone (380 mg, 4.5 mmol) in THF (38 mL) were heated at 50° C. under nitrogen for 3 h. The mixture was cooled, filtered, concentrated in vacuo, and then redissolved in ether (50 mL). The ether solution was washed successively with water (20 mL), saturated aqueous Na$_2$S$_2$O$_5$ (20 mL), saturated aqueous NaCl (20 mL), and water (20 mL), dried and concentrated in vacuo to give a yellow oil (1.025 g) that was used directly in the Hantzsch coupling. This material contained 91% of the desired bromoketone, 5% starting ketone, and 4% 4-bromo-1-butanol, as determined by 1H NMR.

1H NMR (CDCl$_3$) δ ppm: 1.92 (d, 3H, J=7 Hz), 3.96 (s, 3H), 5.28 (q, 1H, J=7 Hz), 8.07 and 8.14 (ABq, 4H)

Step e) 4-[2-(4-tert-Butoxycarbonylpiperazin-1-yl)-5-methylthiazol-4-yl]benzoic acid methyl ester

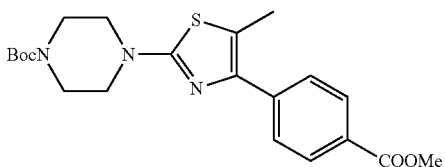 [SMILES: COC(=O)c1ccc(-c2nc(N3CCN(C(=O)OC(C)(C)C)CC3)sc2C)cc1]

All of the α-bromoketone above and 4-thionocarbonylpiperazine-1-carboxylic acid tert-butyl ester (J. Med. Chem., 1998, 5037-5054, 917 mg, 3.73 mmol) were refluxed in 36 mL THF at 70° C. for 2 h, under N$_2$. The precipitate was filtered and the filtrate concentrated in vacuo to give a yellow solid. Flash column chromatography (silica, 5/1 petroleum ether-EtOAc) gave 624 mg of light yellow solids. Chromatography of the precipitate (silica, 2/1 petroleum ether-EtOAc) gave a further 32 mg of compound. Total yield is 44%.

1H NMR (CDCl$_3$) δ ppm: 1.46 (s, 9H), 2.43 (s, 3H), 3.42, (m, 4H), 3.54 (m, 4H), 3.90 (s, 3H), 7.68 and 8.04 (ABq, 4H).

Step f) 4-[2-(4-tert-Butoxycarbonylpiperazin-1-yl)-5-methylthiazol-4-yl]benzoic acid

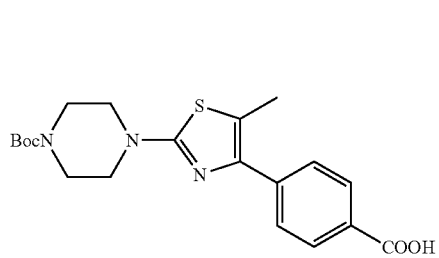 [SMILES: Cc1sc(N2CCN(C(=O)OC(C)(C)C)CC2)nc1-c1ccc(C(=O)O)cc1]

The above methyl ester (564 mg, 1.35 mmol) was heated with 1.35 mL 2N NaOH, 5 mL THF, and 3.65 mL water at 60° C. for 4 h. The reaction mixture was evaporated, poured into 20 mL saturated aqueous NaCl and 20 mL CH$_2$Cl$_2$, and then acidified to pH 3 with 5% citric acid, in an ice bath. The layers were separated and the organic phase was extracted further with 2×10 mL CH$_2$Cl$_2$. The organic phases were combined, washed with water (10 mL), dried, and concentrated in vacuo to give a light yellow solid (537 mg, 98%).

1H NMR (CDCl$_3$) δ ppm: 1.48 (s, 9H), 2.47 (s, 3H), 3.47 (m, 4H), 3.57 (m, 4H), 7.74 and 8.12 (ABq, 4H).

13C NMR (CDCl$_3$) δ ppm: 12.6, 28.3, 42.8, 48.1, 80.3, 119.1, 127.8, 128.2, 130.1, 140.5, 145.6, 154.6, 167.2, 171.4.

LCMS: (M+H)$^+$ 404, (M−H)$^-$ 402.

Step g) 4-[5-methyl-2-(4-methyl-piperazin-1-yl)-thiazol-4-yl]benzoic acid

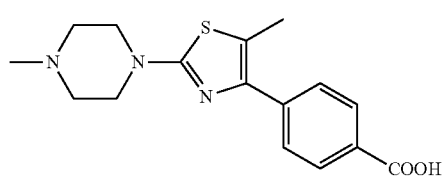 [SMILES: Cc1sc(N2CCN(C)CC2)nc1-c1ccc(C(=O)O)cc1]

4-[4-(4-Carboxyphenyl)-5-methylthiazol-2-yl]-piperazine-1-carboxylic acid tert-butyl ester (0.421 mmol) was dissolved in 4M HCl in 1,4-dioxane, and stirred at room temperature for 1 h. The solvent was then removed in vacuo, and the residue 4-(5-methyl-2-piperazin-1-yl-thiazol-4-yl)-benzoic acid was suspended in methanol (10 mL) and treated with AcOH/AcONa buffer (pH ~5.5, 5 mL), and formaldehyde (0.547 mmol). The reaction mixture was stirred at room temperature for 1 h, then treated with NaCNBH$_3$ (0.547 mmol) and stirred at room temperature overnight. The solvent was then removed under vacuum, and the residue was purified by column chromatography to afford the title compound (0.403 mmol, 95%).

MS (ES) m/z 318 (100%, [M+H]$^+$).

EXAMPLE 4

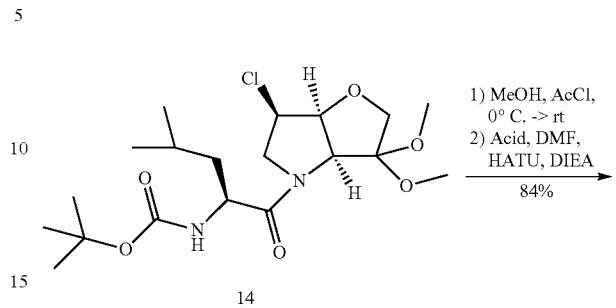

Acetyl chloride (0.4 mL) was added dropwise to a solution of compound 14 (0.121 g, 0.288 mmol) in methanol (4 mL) at 0° C. The reaction mixture was then stirred at room temperature overnight, and then concentrated in vacuo. The residue was redissolved twice in dry DMF (5 mL) and concentrated to dryness, then again dissolved in DMF (6 mL). 4-[5-Methyl-2-(4-methyl-piperazin-1-yl)-thiazol-4-yl]-benzoic acid HCl (112 mg, 0.316 mmol) and DIEA (190 □L, 1.15 mmol) was added to the solution before it was cooled to 0° C. and HATU (120 mg, 0.316 mmol) was added. The reaction was stirred for 3 hours at room temperature before the solvent was removed by rotary evaporation. The crude mixture was dissolved in CHCl$_3$ (15 mL) and washed with 10% citric acid$_{(aq)}$ (10 mL) and NaHCO$_3$ $_{(sat, aq)}$ (10 mL). The organic phase was dried with Na$_2$SO$_4$, filtered and evaporated. The crude product was purified by flash column chromatography (ethyl acetate:acetone 1:1+0.2% TEA) to give the product as a colourless oil/solid in 84% yield (150 mg). LRMS (M+H) 620.

NMR (CDCl$_3$, 400 MHz) for the major rotamer (13:1 mixture of rotamers): 0.98 (d, 3H, J=6.5), 1.04 (d, 3H, J=6.4), 1.55-1.89 (m, 3H), 2.34 (s, 3H), 2.42 (s, 3H), 2.49-2.54 (m, 2H), 3.25 (s, 3H), 3.43 (s, 3H), 3.45-3.51 (m, 3H), 3.72 (d, 1H, J=10.5), 3.91 (d, 1H, J=10.5), 4.05-4.15 (m, 1H), 4.46-4.53 (m, 1H), 4.59 (dd, 1H, J=5.2, 5.1), 4.74 (d, 1H, J=5.6), 4.96-5.04 (m, 1H), 6.83 (d, 1H, J=8.0), 7.68 (d, 2H, J=8.3), 7.79 (d, 2H, J=8.5).

EXAMPLE 5

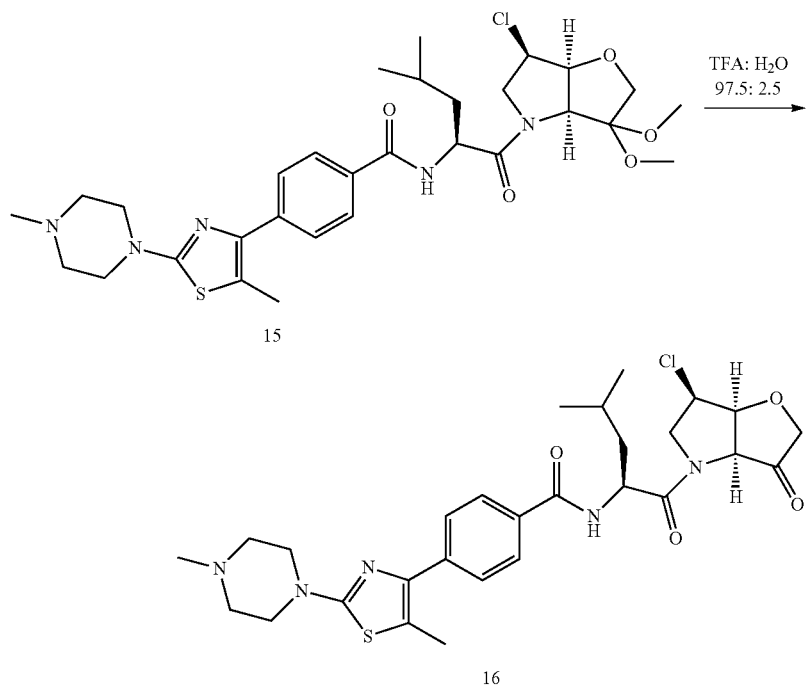

Compound 15 (137 mg, 0.220 mmol) was dissolved in 20 mL of TFA:H₂O (97.5:2.5) and stirred for 4 hours. The solvent was removed in vacuo and the crude product preabsorbed onto silica to be purified by flash column chromatography (EtOAc:Acetone (1:2) with 0.2% TEA) to give the product (lyophilized from dioxane) as an off-white solid in 71% yield (90 mg).

NMR (CDCl₃, 400 MHz) for the major rotamer (10:1 mixture of rotamers): 0.98 (d, 3H, J=6.5), 1.02 (d, 3H, J=6.2), 1.58-1.86 (m, 3H), 2.34 (s, 3H), 2.42 (s, 3H), 2.50-2.54 (m, 2H), 3.44-3.53 (m, 2H), 3.68 (dd, 1H, J=10.4, 8.8), 4.11 (d, 1H, J=17.2), 4.29 (d, 1H, J=17.3), 4.36-4.44 (m, 1H), 4.59 (dd, 1H, J=10.5, 7.1), 4.81 (d, 1H, J=5.8), 4.87-4.97 (m, 2H), 6.83 (d, 1H, J=7.9), 7.68 (d, 2H, J=8.4), 7.79 (d, 2H, J=8.5).

EXAMPLE 6

N-[(S)-1-((3aS,6R,6aS)-6-chloro-3-oxo-hexahydro-furo[3,2-b]pyrrole-4-carbonyl)-3-methyl-butyl]-4-[2-(4-methyl-piperazin-1-yl)-thiazol-4-yl]benzamide

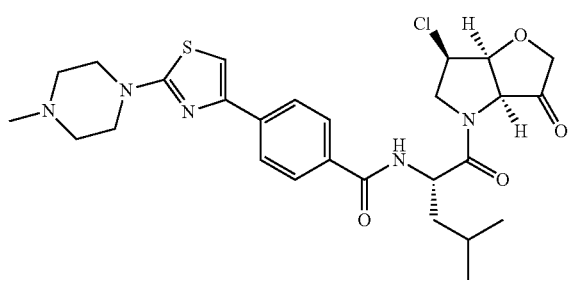 [SMILES: CC(C)C[C@H](NC(=O)c1ccc(-c2csc(N3CCN(C)CC3)n2)cc1)C(=O)N1C[C@@H](Cl)[C@H]2OCC(=O)[C@H]21]

Step a)

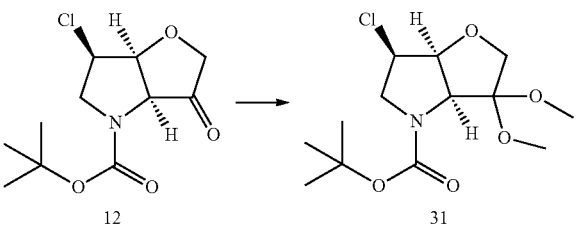 [SMILES: CC(C)(C)OC(=O)N1C[C@@H](Cl)[C@H]2OCC(=O)[C@H]21 ; COC1(OC)CO[C@@H]2[C@H](Cl)CN(C(=O)OC(C)(C)C)[C@@H]21]

To a stirred solution of crude compound 12 (approximately 0.56 mmol) in trimethylorthoformate (0.8 mL) and methanol (3 mL) was added p-toluenesulfonic acid monohydrate (p-TsOH, 0.007 g, 0.037 mmol), then heated to 50° C. overnight. The reaction mixture was then monitored by TLC (3:2 Hexane-ethyl acetate, ninhydrin staining). The reaction mixture was heated to 60° C. and a total of 21 mg p-TsOH was added over 4 h which gave the Boc-deprotected ketal as the major product (as indicated by TLC). The reaction mixture was then cooled to room temperature and triethylamine (0.32 mL, 2.24 mmol) was added followed by di-tert-butyl dicarbonate (0.184 g, 0.84 mmol). The reaction mixture was kept at room temperature for 2.5 h, then concentrated in vacuo and preabsorbed onto silica. Flash column chromatography of the residue (stepwise gradient elution, ethyl acetate in hexane, 20-25%) followed by concentration in vacuo of the appropriate fractions and removal of residual solvent by further drying on a vacuum line overnight gave the product 31 as an off-white solid (0.069 g, 0.022 mmol, 40% over 2 steps).

NMR data (400 MHz, 298 K, CDCl₃): ¹H, □ 1.47 (s, 9 H), 3.16 (m, 1 H), 3.30 (s, 3 H), 3.37 (s, 3 H), 3.72 (d, 1 H, J=9.3 Hz), 3.86 (m, 1 H), 3.98 (m, 1 H), 4.15 (m, 1 H), 4.44 (d, 1 H, J=5.4 Hz), 4.61 (m, 1 H).

Step b)

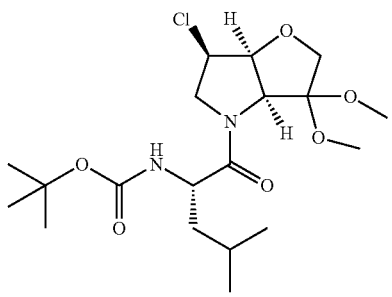

32b

To a stirred solution of compound 31 (0.074 g, 0.24 mmol) in methanol (2.7 mL) at 0° C. was added dropwise acetyl chloride (0.3 mL) over 1 minute. The reaction mixture was monitored by TLC (Hexane-ethyl acetate 3:2 and dichloromethane-methanol 95:5, ninhydrin staining) and after 4.5 h the starting material was completely consumed. The reaction mixture was then concentrated in vacuo, then redissolved in dioxane with a few drops of H₂O and lyophilized. The obtained off-white amorphous solid and N-(tert-butoxycarbonyl)-L-leucine monohydrate (0.066 g, 0.26 mmol) was dissolved in DMF (3 mL) and concentrated in vacuo. The residue was then redissolved in DMF (3 mL) and N-ethyldiisopropylamine (0.13 mL, 0.72 mmol) added. To this solution was added N—O-(7-azabenzotriazol-1-yl)-N,N,N',N'-tetramethyluronium hexafluorophosphate (HATU, 0.12 g, 0.31 mmol) at 0° C. The reaction mixture was kept at 0° C. for 40 min, and an additional 75 min at rt. The reaction mixture was then diluted with ethyl acetate (25 mL), washed successively with aq. 10% citric acid (3×15 mL) and aq. saturated sodium hydrogen carbonate (3×15 mL) and then dried (sodium sulfate), filtered and concentrated in vacuo. Flash column chromatography on silica gel of the residue using 2:1 hexane-ethyl acetate as eluant, followed by concentration in vacuo of the appropriate fractions gave the compound 32b as a colorless syrup (0.089 g, 0.21 mmol, 88%) which was used directly in the next step.

Step c

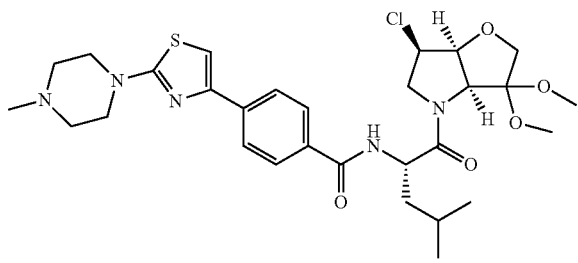

32c

To a solution of compound 32b (0.089 g, 0.21 mmol) in methanol (2.7 mL) at 0° C. was added dropwise acetyl chloride (0.3 mL) over 0.5 minutes. The reaction mixture was then stirred at rt for 5.5 h (monitored by TLC:dichloromethane-methanol 95:5, staining using ammoniummolybdate-cerium sulfate in aq. 10% sulfuric acid), and then concentrated in vacuo. The residue was redissolved in dioxane (5 mL) and a small amount of water was added, and then the solution was lyophilized. The obtained colorless amorphous solid and 4-[2-(4-methyl-piperazin-1-yl)thiazol-4-yl]benzoic acid HBr salt (0.089 g, 0.23 mmol) was dissolved in DMF (3 mL) and N-ethyldiisopropylamine (0.15 mL, 0.85 mmol) then added and the solution cooled to 0° C. and HATU (0.105 g, 0.275 mmol) added. The reaction mixture was stirred at 0° C. for 1 h and an additional 1 h at rt (monitored by TLC:dichloromethane-methanol 95:5, visualized by UV-light and staining using ammoniummolybdate-cerium sulfate in aq. 10% sulfuric acid). The reaction mixture was then diluted with ethyl acetate (25 mL), washed with 3:1 aq. saturated sodium hydrogen carbonate/brine (3×20 mL), then dried (sodium sulfate), filtered and concentrated in vacuo. Flash column chromatography of the residue using stepwise gradient elution (methanol in dichloromethane, 0-5%) followed by concentration in vacuo of the appropriate fractions and lyophilization from dioxane (5 mL) and a few drops of water, gave the product 32c as a colorless amorphous solid (0.121 g, 0.20 mmol, 94%).

Step d)

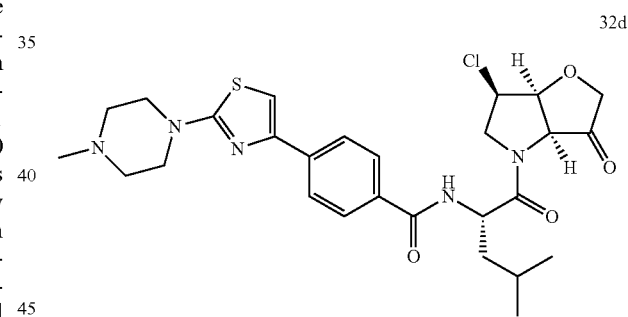

32d

To 32c (0.114 g, 0.188 mmol) was added a solution of 97.5:2.5 TFA-water (6 mL) at rt, the obtained solution was monitored by LC-MS and after stirring for 2 h at rt the reaction mixture was concentrated in vacuo. The residue was redissolved in ethyl acetate (25 mL), washed with aq. saturated sodium hydrogen carbonate (3×15 mL) and brine (1×15 mL), then dried (sodium sulfate), filtered and concentrated in vacuo. The residue obtained as an amorphous solid was dissolved in DMSO-acetonitrile-water-dioxane (approx. 12 mL) and purified by preparative HPLC-MS (Column: Sunfire 19×100 mm ($C_{18}$), eluent A: 10 mM ammonium acetate in water, eluent B: 10 mM ammonium acetate in 9:1 acetonitrile-water, gradient: 30% B to 80% B in 8 minutes, flow: 20 mL/min). Appropriate fractions were concentrated in vacuo. The residue was redissolved in dioxane with some drops of water, frozen and lyophilized, affording compound 32d as an off-white yellow amorphous solid (0.055 g, 0.10 mmol, 52%). An aliquot of the obtained product was dissolved in CDCl₃ and analyzed by NMR, which indicated the product exits in the ketoform (hydrate form undetectable) in a 9:1 mixture of rotamers. NMR data refers to the major rotamer. When analyzed by HPLC-MS, the hydrate form is the major form.

NMR data (500 MHz, 293 K, CDCl$_3$): $^1$H, □ 0.96 (d, 3 H, CH$_3$—CH), 1.02 (d, 3 H, CH$_3$—CH) 1.62-1.78 (m, 3 H, CH(CH$_3$)$_2$ and CH$_2$CH(CH$_3$)$_2$), 2.37 (s, 3 H, CH$_3$—N), 2.56 (m, 4 H, 2×CH$_2$—N), 3.59 (m, 4 H, 2×CH$_2$—N), 3.70 (m, 1 H, CHH—CHCl), 4.13 (d, 1 H, CHH—O), 4.31 (d, 1H, CHH—O), 4.42 (m, 1 H, CHCl), 4.60 (m, 1 H, CHH—CHCl), 4.82 (m, 1 H, CHCl—CH), 4.90-4.96 (m, 2 H, CH—C=O and CHNH), 6.85-6.89 (m, 2 H, NH and thiazole-H), 7.78 (d, 2 H, Ar—H), 7.89 (d, 2 H, Ar—H). LR-MS: Calcd for C$_{27}$H$_{35}$ClN$_5$O$_4$S: 560.2. Found: 560.3 [M+H], Calcd for C$_{27}$H$_{37}$ClN$_5$O$_5$S: 578.2. Found: 578.3.

EXAMPLE 7

N-[2-((3aS,6R,6aS)-6-Chloro-3-oxo-hexahydro-furo[3,2-b]pyrrole-4-yl)-1-S-cyclohexyl-2-oxo-ethyl]-4-[2-(4-methyl-piperazin-1-yl)-thiazol-4-yl]-benzamide

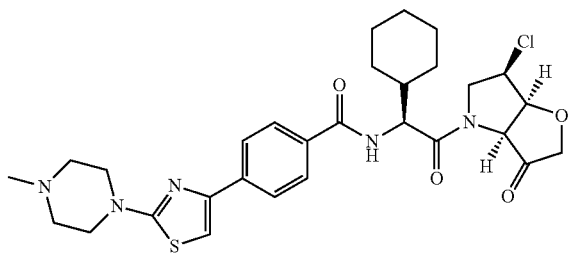 [SMILES: CN1CCN(c2nc(-c3ccc(C(=O)N[C@H](C(=O)N4C[C@@H](Cl)[C@H]5OCC(=O)[C@H]54)C4CCCCC4)cc3)cs2)CC1]

Step a) [2-((3aS,6R,6aS)-6-Chloro-3,3-dimethoxy-hexahydro-furo[3,2-b]pyrrol-4-yl)-1-S-cyclohexyl-2-oxo-ethyl]-carbamic acid tert-butyl ester (7a)

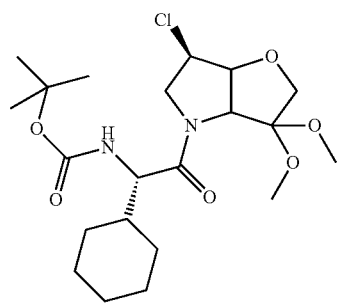 [SMILES: COC1(OC)COC2C1N(C(=O)[C@@H](NC(=O)OC(C)(C)C)C1CCCCC1)C[C@H]2Cl]

The HCl salt of (3aS,6R,6aS)-6-chloro-3,3-dimethyoxy-hexahydro-furo[3,2-b]pyrrole (13) (0.23 mmol) and Boc-cyclohexyl-Gly-OH (64.4 mg, 0.25 mmol) were coevaporated from DMF, redissolved in 3 mL DMF, and cooled in an ice bath. DIEA (160 □L, 0.92 mmol), followed by HATU (108 mg, 0.28 mmol) were added. After 20 mins, the mixture was stirred at RT for 2 h 20 min, and concentrated under vacuum. The residue was dissolved in EtOAc (10 mL), washed successively with 10% citric acid (5 mL), saturated NaHCO$_3$ (5 mL), and saturated NaCl (2×5 mL). The organic phase was dried (Na$_2$SO$_4$) and concentrated. Flash column chromatography (silica, 2/1 pentane-EtOAc) gave a white solid (86.6 mg, 84% yield).

LCMS [M+23]$^+$=469

Step b) N-[2-((3aS,6R,6aS)-6-Chloro-3,3-dimethoxy-hexahydro-furo[3,2-b]pyrrole-4-yl]-1-S-cyclohexyl-2-oxo-ethyl]-4-[2-(4-methyl-piperazin-1-yl)-thiazol-4-yl]-benzamide (7b)

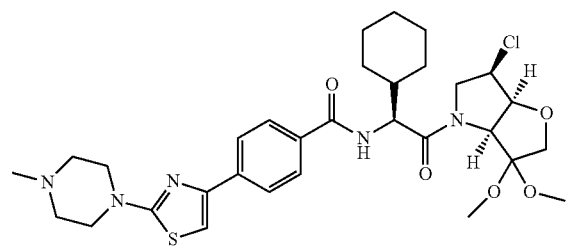

Acetyl chloride (0.25 mL) was added to an ice-cooled solution of the carbamic acid tert-butyl ester above (86.6 mg, 0.194 mmol) in methanol (2.20 mL). The mixture was stirred at RT for 3 h 45 min and evaporated. Freeze drying from dioxane-water gave the deprotected amine HCl salt which was then first coevaporated from DMF with 4-[2-(4-methyl-piperazin-1-yl)thiazol-4-yl]benzoic acid HBr salt (83 mg, 0.22 mmol) and then redissolved in 2.5 mL DMF. The mixture was cooled in an ice bath, DIEA (140 □L, 0.80 mmol) was added, followed by HATU (83.8 mg, 0.22 mmol). After 15 mins, the mixture was stirred at RT for 2.5 h. The mixture was concentrated, dissolved in EtOAc (20 mL), washed successively with saturated NaHCO$_3$ (10 mL) and saturated NaCl (2×10 mL). The organic phase was dried (Na$_2$SO$_4$) and concentrated. Flash column chromatography (silica, CH$_2$Cl$_2$—MeOH-Et$_3$N)) gave white solids (121.2 mg, 99% yield).

LCMS [M+1]$^+$=632

Step c) N-[2-((3aS,6R,6aS)-6-Chloro-3-oxo-hexahydro-furo[3,2-b]pyrrole-4-yl)-1-S-cyclohexyl-2-oxo-ethyl]-4-[2-(4-methyl-piperazin-1-yl)-thiazol-4-yl]-benzamide (7c)

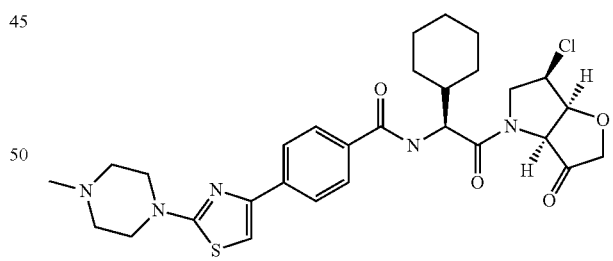

The dimethoxy ether above (115 mg, 0.182 mmol) was deprotected in a solution of TFA-water (97.5:2.5 v/v, 6.0 mL) by stirring at RT for 2 h 15 min. The mixture was concentrated, dissolved in EtOAc (25 mL), washed successively with saturated NaHCO$_3$ (3×15 mL) and saturated NaCl (15 mL). The organic phase was dried (Na$_2$SO$_4$) and evaporated. The crude material was purified by HPLC-MS (column Sunfire PrepC$_{18}$OBD 5 □m 19×100 mm; gradient 60 to 80% B in A, mobile phases A 10 nM NH$_4$OAc in water and B 10 mM NH$_4$OAc in 90% MeCN) to give the final compound as a white solid (63 mg, 59% yield).

LCMS ES$^+$=604 (hydrate) and ES$^+$=586 (ketone)

1H NMR (500 MHz, CDCl₃) ppm 7.90 and 7.78 (ABq, 2H each, 6.89 (s, 1H), 6.83 (d, 1H, NH), 4.91 (m, 1H), 4.86 (m, 1H), 4.69 (m, 1H), 4.62 (dd, 1H), 4.40 (m, 1H), 4.32 and 4.14 (ABq, 1H each), 3.72 (dd, 1H), 3.60 (m, 4H), 2.58 (m, 4H), 2.38 (s, 3H), 2.10-1.04 (m, 11H)

EXAMPLE 8

N-[(S)-1-((3aS,6R,6aS)-6-chloro-3-oxo-hexahydro-furo[3,2-b]pyrrole-4-carbonyl)-3-fluoro-3-methyl-butyl]-4-[2-(4-methyl-piperazin-1-yl)-thiazol-4-yl] benzamide

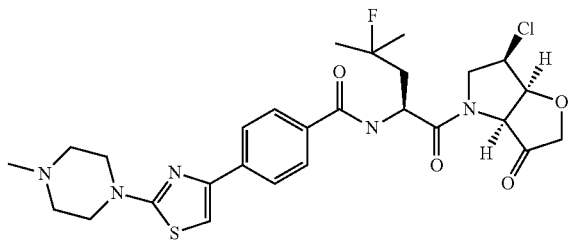 [SMILES: CN1CCN(c2nc(-c3ccc(C(=O)N[C@@H](CC(C)(C)F)C(=O)N4C[C@@H](Cl)[C@H]5OCC(=O)[C@H]54)cc3)cs2)CC1]

Step a)

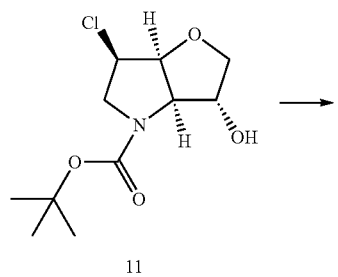

11

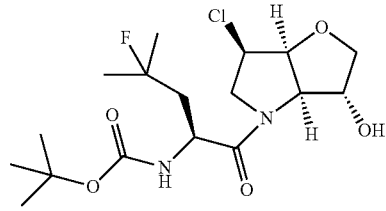

42

Acetyl chloride (0.4 mL) was added dropwise to a solution of compound 11 (60 mg, 0.228 mmol) in methanol (4 mL) at 0° C. The reaction mixture was stirred at room temperature for 6 hrs, concentrated, redissolved in 1,4-dioxane and freeze dried over night. The residue was dissolved in 5 mL of DMF. □-fluoro-BOC-Leu-OH (Truong et al SynLett 2005 No 8 1279-1280, 50 mg, 0.201 mmol) and DIEA (133 □L, 0.802 mmol) was added to the solution before it was cooled to 0° C. and HATU (80 mg, 0.211 mmol) was added. The reaction was stirred for 3 hours at room temperature before the solvent was concentrated in vacuo. The product was dissolved in EtOAc (20 mL) and washed with NaHCO₃ (sat, aq) (10 mL). The organic phase was dried with Na₂SO₄, filtered and concentrated in vacuo. The product was purified by flash chromatography (ethyl acetate) to give the product 42 in 99% yield (79 mg).

Step b)

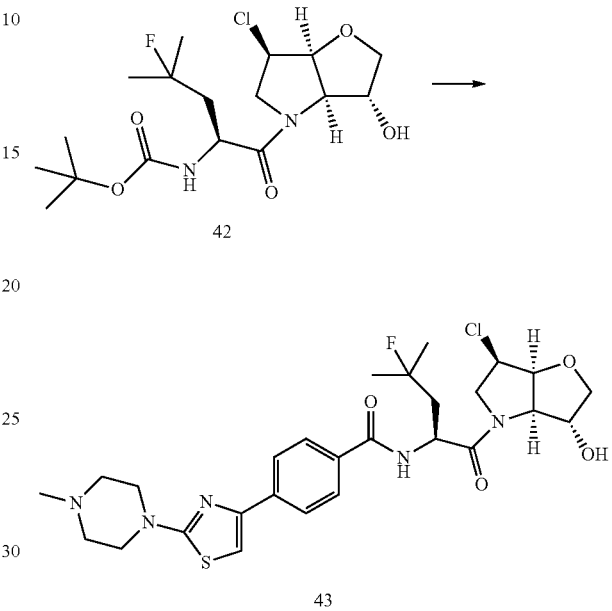

42

43

Acetyl chloride (0.4 mL) was added dropwise to a solution of compound 42 (79 mg, 0.199 mmol) in methanol (4 mL) at 0° C. The reaction mixture was stirred at room temperature for 6 hrs, concentrated, redissolved in 1,4-dioxane and freeze dried over night. The residue was dissolved in 5 mL of DMF. 4-[2-(4-methyl-piperazin-1-yl)-thiazol-4-yl]-benzoic acid HBr (76 mg, 0.198 mmol). DIEA (119 □L, 0.721 mmol) was added to the solution before it was cooled to 0° C. and HATU (72 mg, 0.189 mmol) was added. The reaction was stirred for 3 hours at room temperature before the solvent was removed in vacuo. The product was dissolved in CHCl₃ (15 mL) and washed with NaHCO₃ (sat, aq) (10 mL). The organic phase was dried with Na₂SO₄, filtered and evaporated. The product was purified by flash chromatography (chloroform:ethanol 7:3+ 0.1% TEA) to yield adequately pure 43 which could be used direct in the next step.

Step c)

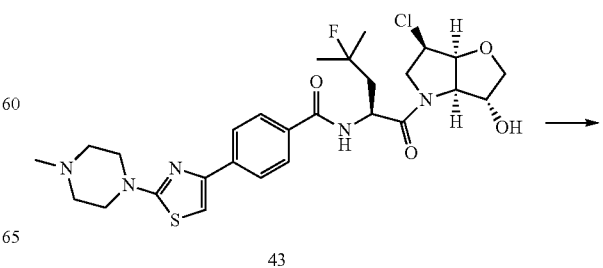

43

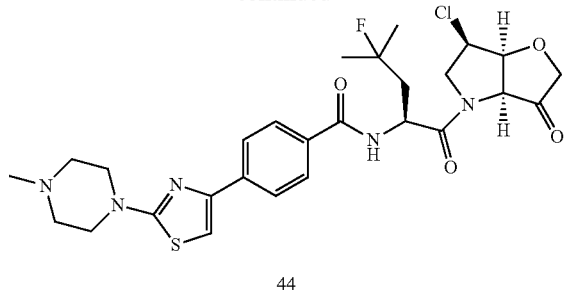

44

Compound 43 (104 mg, 0.198 mmol) (not pure) was dissolved in 9 mL of DCM:DMSO (2:1). TEA (111 □L, 0.797 mmol) was added followed by SO$_3$*pyridine (48 mg, 0.299 mmol). The reaction was stirred at room temperature and monitored by LC-MS. After 4 hrs, another portion (48 mg) of SO$_3$*pyridine was added and after 4 more hours yet another portion. After 22 hrs (over night) a further portion was added and after 2 more hours a finishing portion was added. The solution was poured into a separating funnel with 40 mL of DCM and washed with 20 mL of NaHCO$_3$ $_{(sat, aq)}$. The organic phase was dried with Na$_2$SO$_4$, filtered and concentrated in vacuo. The product was purified by semi-preparative HPLC on a Sunfire C18 column with mobile phases A (90:10 H$_2$O:acetonitrile, 10 mM NH$_4$Ac) and B (10:90 H$_2$O:acetonitrile, 10 mM NH$_4$Ac) going from 40-75% B. The product was obtained as an off-white solid in 29% yield (30 mg).

NMR (CDCl$_3$, 400 MHz): 1.37-1.52 (m, 6H), 2.10-2.30 (m, 2H), 2.37 (s, 3H), 2.58-2.63 (m, 2H), 3.57-3.62 (m, 2H), 3.73 (dd, 1H, J=10.5, 8.7), 4.10 (d, 1H, J=16.9), 4.28 (d, 1H, J=16.9), 4.43-4.50 (m, 1H), 4.71 (dd, 1H, J=10.6, 6.9), 4.78 (d, 1H, J=6.0), 4.87-4.93 (m, 1H), 4.95-5.03 (m, 1H), 6.86 (s, 1H), 7.37 (d, 1H, J=7.3), 7.73 (d, 2H, J=8.3), 7.82 (d, 2H, J=8.6). LRMS (M+H) 578.

EXAMPLE 9

An alternative P3 building block

3-Fluoro-4-[2-(4-methylpiperazin-1-yl)-thiazol-4-yl]benzoic acid HCl salt

Step a) Methyl 4-bromo-3-fluorobenzoate (9a)

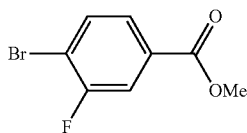

4-Bromo-3-fluorobenzoic acid (2.46 g, 11.2 mmol) was dissolved in MeOH (9 mL) and toluene (4 mL) and cooled in an ice bath. (Trimethylsilyl)diazomethane (11 mL, 2.0 M in hexanes, 22 mmol) was added dropwise until the yellow color persisted. The solution was stirred at room temperature for 40 mins and then concentrated in vacuo. A second batch of carboxylic acid (2.43 g) was treated similarly. The crude product from both batches were combined and subjected to flash chromatography (silica, 5/1 pentane-EtOAc) to give the methyl ester as white solids (4.92 g, 95% yield).

$^1$H NMR (400 MHz, CDCl$_3$) delta ppm 7.77 (m, 1H), 7.71 (m, 1H), 7.64 (m, 1H), 3.93 (s, 3H).

Step b) Methyl 4-acetoxy-3-fluorobenzoate (9b)

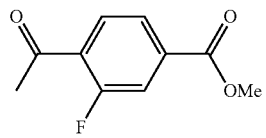

Allyl chloride (105 µL, 1.28 mmol) and TFA (20 µL, 0.26 mmol) were added to a suspension of zinc dust (480 mg, 7.34 mmol) and anhydrous cobalt(II) bromide (96.6 mg, 0.44 mmol) in MeCN (4 mL), under inert gas. After stirring at room temperature for 10 min, the aryl bromide (1.003 g, 4.30 mmol dissolved in 5 mL MeCN) from (a) was added, followed by acetic anhydride (0.45 mL, 4.79 mmol) and more MeCN (1 mL). The mixture was stirred overnight, quenched with 1M HCl (20 mL), and then extracted with EtOAc (3×20 mL). The organic phase was washed successively with saturated aqueous NaHCO$_3$ (20 mL) and saturated NaCl (2×20 mL), dried (Na$_2$SO$_4$), and concentrated. Flash chromatography (silica, 6/1 to 4/1 petroleum ether-EtOAc gave recovered bromide (161.1 mg, 16%) and the desired ketone (white solids, 305.5 mg, 36%).

NMR (CDCl$_3$) delta ppm: $^1$H (400 MHz) 7.94-7.86 (m, 2H), 7.80 (dd, 1H, J=11.2, 1.6 Hz), 3.95 (s, 3H), 2.67 (d, 3H, J=4.4 Hz); $^{19}$F (376 MHz)-109.2 (m); $^{13}$C (100 MHz) 195.4 (d, J=3.7 Hz), 165.1 (d, J=2.2 Hz), 161.6 (d, J=255 Hz), 135.8 (d, J=8.1 Hz), 130.7 (d, J=2.9 Hz), 129.0 (d, J=14 Hz), 125.2 (d, J=3.6 Hz), 117.9 (d, J=26 Hz), 52.7 (s), 31.4 (d, J=7.3 Hz).

Step c) Methyl 4-(2-bromoacetoxy)-3-fluorobenzoate (9c)

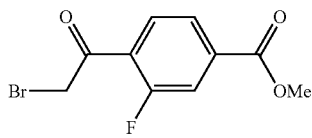 [SMILES: COC(=O)c1ccc(C(=O)CBr)c(F)c1]

THF (10 mL) and 2-pyrrolidinone (91 µL, 1.20 mmol) were added to a mixture of the ketone from b) (198 mg, 1.01 mmol) and pyrrolidone hydrotribromide (532 mg, 1.07 mmol). After heating at 60-65° C. for 2 h, the mixture was concentrated under vacuum and then partitioned between EtOAc (20 mL) and saturated Na$_2$S$_2$O$_3$ (10 mL). The aqueous phase was extracted with EtOAc (10 mL). The organic phases were combined, washed with saturated NaCl (2×10 mL), dried (Na$_2$SO$_4$), and concentrated. Flash chromatography (silica, 7/1 petroleum ether—EtOAc) gave white solids (0.2634 g) containing 84% of the desired bromide (as determined by integration of $^{19}$F NMR peaks).

NMR (CDCl$_3$) δ ppm: $^1$H (400 MHz) 7.93 (m, 1H), 7.88 (m, 1H), 7.79 (dd, 1H, J=11.2, 1.6 Hz), 4.50 (d, 2H, J=2.4 Hz), 3.94 (s, 3H); $^{19}$F (376 MHz)-108.4 (m).

Step d) Methyl 3-fluoro-4-[2-(4-methylpiperazin-1-yl)-thiazol-4-yl]benzoate (9d)

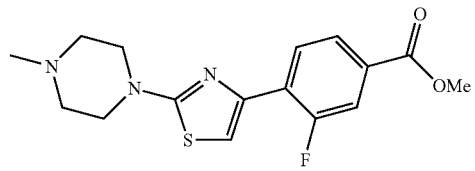 [SMILES: COC(=O)c1ccc(-c2csc(N3CCN(C)CC3)n2)c(F)c1]

EtOH (5.0 mL) was added to the bromoketone above (193 mg, 0.70 mmol) and 4-methyl-piperazine-1-carbothioic acid amide (113 mg, 0.71 mmol) and the mixture was heated at 70° C. for 2 h 15 min. The precipitates were filtered, washed with cold EtOH, and dried under vacuum and characterized. The procedure was repeated in a larger scale for 1.75 g bromoketone (6.36 mmol).

NMR (1/1 CDCl$_3$–CD$_3$OD) δ ppm: $^1$H (400 MHz) 8.20 (m, 1H), 7.86 (dd, 1H, J=8.4, 1.6 Hz), 7.76 (dd, 1H, J=11.4, 1.8 Hz), 7.38 (d, 1 H, J=2.4 Hz), 4.23 (br, 2H), 3.95, (s, 3H), 3.65 (br, 4H), 3.32 (br, 2H), 2.98 (s, 3H); $^{19}$F (376 MHz)-114.0 (m). LCMS 1[M+H]$^+$=336.

The precipitates from both preparations were combined and suspended in saturated NaHCO$_3$ (50 mL). The mixture was extracted with EtOAc. The organic phase was washed with water, dried (Na$_2$SO$_4$), and evaporated to give the title compound as cream solids (1.76 g).

Step e) 3-fluoro-4-[2-(4-methylpiperazin-1-yl)-thiazol-4-yl]benzoic acid HCl salt (9e)

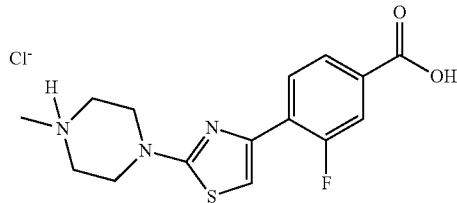

The methyl ester (1.76 g, 5.25 mmol) (9d) was heated at 80° C. with 6M HCl (40 mL) for 5.5 h. More 6M HCl (10 mL) was added and the mixture was heated at 90° C. for 1 h 15 min. After cooling, the mixture was then evaporated under vacuum and freeze-dried from water to give the final product as cream solids in quantitative yield.

NMR (DMSO-d6) δ ppm: $^1$H (400 MHz) 11.60 (br, 1H), 8.18 (t, 1H, J=8.0 Hz), 7.82 (dd, 1H, J=8.4, 1.6 Hz), 7.72 (dd, 1H, J=12.0, 1.6 Hz), 7.48 (d, 1H, J=2.8 Hz), 4.11 (m, 2H), 3.58 (m, 2H), 3.49 (m, 2H), 3.19 (m, 2H), 2.80 (d, 3H, J=4.4 Hz); $^{19}$F (376 MHz)-113.5 (m); $^{13}$C (100 MHz) 168.9, 166.0, 159.0 (d, J=250 Hz), 143.4, 131.4 (d, J=8 Hz), 129.8, 125.8 (d, J=11 Hz), 125.6, 116.6 (d, J=24 Hz), 111.1 (J=15 Hz), 51.1, 45.0, 41.9. LCMS [M+H]$^+$=322.

EXAMPLE 10

N-[(S)-1-((3aS,6R,6aS)-6-Chloro-3-oxo-hexahydro-furo[3,2-b]pyrrole-4-carbonyl)-3-methyl-butyl]-3-fluoro-4-[2-(4-methyl-piperazin-1-yl)-thiazol-4-yl]-benzamide

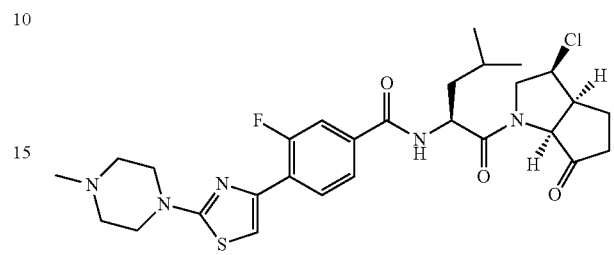

Step a) N-[(S)-1-((3S,3aS,6R,6aS)-6-Chloro-3-hydroxy-hexahydro-furo[3,2-b]pyrrole-4-carbonyl)-3-methyl-butyl]-3-fluoro-4-[2-(4-methyl-piperazin-1-yl)-thiazol-4-yl]-benzamide

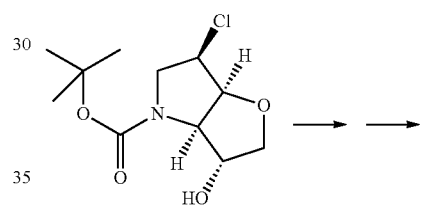

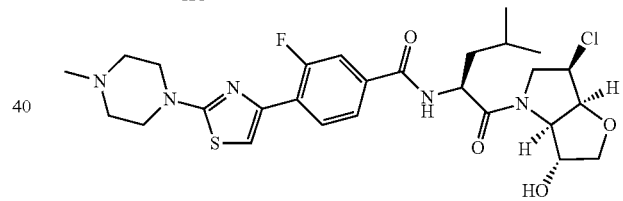

This compound was prepared from N-[(S)-1-((3S,3aS,6R,6aS)-6-chloro-3-hydroxy-hexahydro-furo[3,2-b]pyrrole-4-carboxylic acid tert-butyl ester by a series of deprotection (acetyl chloride, MeOH) and HATU-mediated coupling steps with Boc-leucine initially, and finally 3-fluoro-4-[2-(4-methylpiperazin-1-yl)-thiazol-4-yl]benzoic acid HCl salt prepared as described in Example 9.

LCMS: [M+H]$^+$=580; [M−H]$^-$=578. $^{19}$F NMR (376 MHz, CDCl$_3$+CD$_3$OD) delta ppm −113.3 (m).

Step b)

Triethylamine (20 μL) and sulfur trioxide-pyridine complex (20 mg, 0.125 mmol) were added to a solution of the alcohol (16.6 mg, 0.03 mmol) from (a) in 0.9 mL CH$_2$Cl$_2$ and 0.45 mL DMSO and stirred at rt. After 2 h, more triethylamine (10 μL) and sulfur trioxide-pyridine complex (10 mg) were added and the mixture was stirred overnight to complete oxidation to the ketone. The mixture was diluted with CH$_2$Cl$_2$ and washed with saturated NaHCO$_3$ followed by saturated aqueous NaCl. The organic phase was dried (Na$_2$SO$_4$) and evaporated to give an oil. The crude material was purified by HPLC-MS (column Sunfire PrepC$_{18}$ um 19×100 mm; OBD 5 gradient 30 to 80% B in A, mobile phases A 10 mM NH$_4$OAc in water and B 10 mM NH$_4$OAc in 90% MeCN) to give the title compound as white solids (4.4 mg).

NMR (CDCl$_3$) delta ppm: $^1$H (500 MHz, 2 rotamers observed, major rotamer described) 8.22 (m, 1H, phenyl H5), 7.56-7.54 (m, 2H, phenyl H2 and H6), 7.21 (m, 1H, thiazole), 6.81 (d, 1H, J=8.5 Hz, NH), 4.94-4.85 (m, 2H, NHCHC=O and ClCCHO), 4.84 (d, 1H, J=6.0 Hz, (O=C)NCHC=O)), 4.56 (dd, 1H, J=10.5, 7.0 Hz), 4.42 (m, 1H, C1CH), 4.32 and 4.14 (ABq, 1H each), 3.70 (dd, 1H, J=10, 9 Hz), 3.59 (m, 4H), 2.57 (m, 4H), 2.37 (s, 3H, NMe), 1.8-1.6 (m, 3H, CH$_2$CHMe$_2$), 1.03 (d, 3H, J=6.0 Hz, i-Pr), 0.96 (d, 3H, J=6.5 Hz, i-Pr); $^{19}$F (376 MHz) −112.9 (m, major rotamer, 84%) and −113.2 (m, minor, 16%).

LCMS: monoisotopic mol mass 577.4 Da; ES+=578.4 (M+H)$^+$, 596.5 [M+H$_2$O+H]$^+$.

EXAMPLE 11

An alternative P3/P2 building block

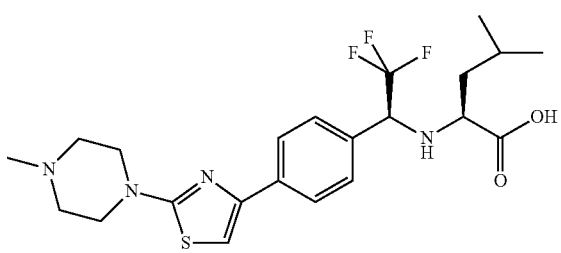 [SMILES: CC(C)C[C@H](N[C@@H](c1ccc(-c2csc(N3CCN(C)CC3)n2)cc1)C(F)(F)F)C(=O)O]

Step a) (S)-2-[(S)-1-(4-Bromo-phenyl)-2,2,2-trifluoro-ethylamino]-4-methyl-pentanoic acid isopropyl ester (11a)

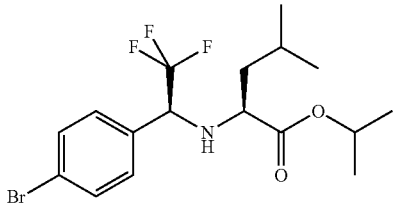 [SMILES: CC(C)C[C@H](N[C@@H](c1ccc(Br)cc1)C(F)(F)F)C(=O)OC(C)C]

To a stirred solution of (S)-2-[(S)-1-(4-bromo-phenyl)-2,2,2-trifluoro-ethylamino]-4-methyl-pentanoic acid, prepared as shown in Li, C. S. et al *Bioorg. Med. Chem. Lett.* 2006, 16, 1985, (1.80 g, 4.9 mmol) in isopropyl alcohol (100 mL) was added concentrated sulphuric acid (2 mL). The resulting solution was heated at 80° C. for 4 hours. The reaction mixture was allowed to cool and was then concentrated in vacuo. The resulting oil was dispersed in CH$_2$Cl$_2$ (100 mL), washed with saturated NaHCO$_3$ (2×50 mL), dried (MgSO$_4$) and concentrated in vacuo to yield the title compound as a brown oil (1.77 g, 88%). MS [M+H] 412.

Step b) (S)-4-Methyl-2-{(S)-2,2,2-trifluoro-1-[4-(4,4,5,5-tetramethyl-[1,3,2]dioxaborolan-2-yl)-phenyl]-ethylamino}-pentanoic acid isopropyl ester (11b)

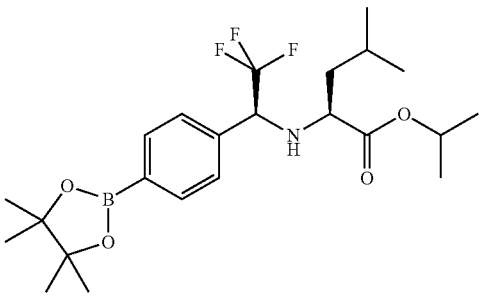 [SMILES: CC(C)C[C@H](N[C@@H](c1ccc(B2OC(C)(C)C(C)(C)O2)cc1)C(F)(F)F)C(=O)OC(C)C]

To a stirred solution of the bromoderivative 1k (2.2 g, 5.36 mmol) in DMF (30 mL) was added bis (pinacolato) boron (2.0 g, 8.04 mmol), potassium acetate (1.6 g 16.1 mmol) and [1,1'-bis(diphenylphosphino)ferrocene]palladium(II) chloride 1:1 complex with CH$_2$Cl$_2$ (0.438 g, 0.54 mmol). The resulting solution was sealed in a tube and heated in a microwave to 160° C. for 20 minutes. The reaction mixture was allowed to cool to room temperature and was then filtered through a short silica column eluted with ethyl acetate (500 mL). The resulting solution was concentrated in vacuo and the crude product was purified by reverse phase C18 column chromatography (H$_2$O:MeCN, 50-100% gradient) to yield the title compound as a brown oil (0.920 g, 38%). MS [M+H] 458.

Step c) (S)-4-Methyl-2-((S)-2,2,2-trifluoro-1-{4-[2-(4-methyl-piperazin-1-yl)-thiazol-4-yl]-phenyl}-ethylamino)-pentanoic acid isopropyl ester (11c)

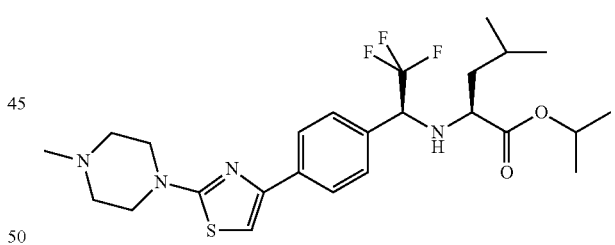

To a stirred solution of the borolane derivative 1k (0.72 g, 1.57 mmol) in DMF:H$_2$O (1:1, 20 mL) was added 1-(4-bromo-thiazol-2-yl)-4-methyl-piperazine (0.5 g, 1.89 mmol), sodium carbonate (0.2 g 1.89 mmol) and [1,1'-bis(diphenylphosphino)ferrocene]palladium(II) chloride 1:1 complex with CH$_2$Cl$_2$ (0.129 g, 0.16 mmol). The resulting solution was sealed in a tube and heated in a microwave to 160° C. for 20 minutes. The reaction mixture was allowed to cool and was then diluted with CH$_2$Cl$_2$ (100 mL). The organic phase was separated, dried (MgSO$_4$) and concentrated in vacuo. The crude product was purified by flash column chromatography (ethyl acetate:MeOH, 9:1) to yield the title compound as a dark red solid (0.150 g, 13%). MS [M+H] 513. Retention time 4.0 mins 50-97 10 mM (NH$_3$)$_2$CO$_3$:MeCN 6 min Gradient C12 Reverse Phase.

Step d) (S)-4-Methyl-2-((S)-2,2,2-trifluoro-1-{4-[2-(4-methyl-piperazin-1-yl)-thiazol-4-yl]-phenyl}-ethylamino)-pentanoic acid; hydrogen chloride (11d)

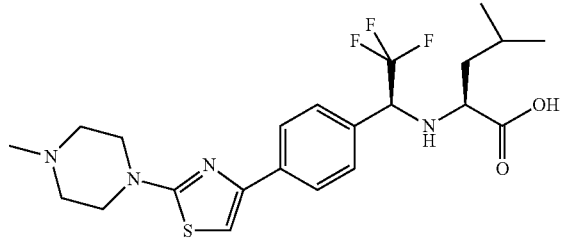 [SMILES: CC(C)C[C@H](N[C@@H](c1ccc(-c2csc(N3CCN(C)CC3)n2)cc1)C(F)(F)F)C(=O)O]

To a stirred mixture of 2M hydrochloric acid and dioxane (1:1, 10 mL) was added (S)-4-methyl-2-((S)-2,2,2-trifluoro-1-{4-[2-(4-methyl-piperazin-1-yl)-thiazol-4-yl]-phenyl}-ethylamino)-pentanoic acid isopropyl ester (0.15 g, 0.29 mmol), prepared as described by Palmer et al. in *J. Med. Chem.* 2005, 48, 7520-7534. The solution was heated for 20 hours at 100° C. and then concentrated in vacuo to give the title compound as a dark brown solid (0.14 g, 98%) which can be coupled to the P1 building block and the ketone regenerated by any of the methods described above, typically without further purification. MS M−H 469.

EXAMPLE 11A

An alternative P3 building block

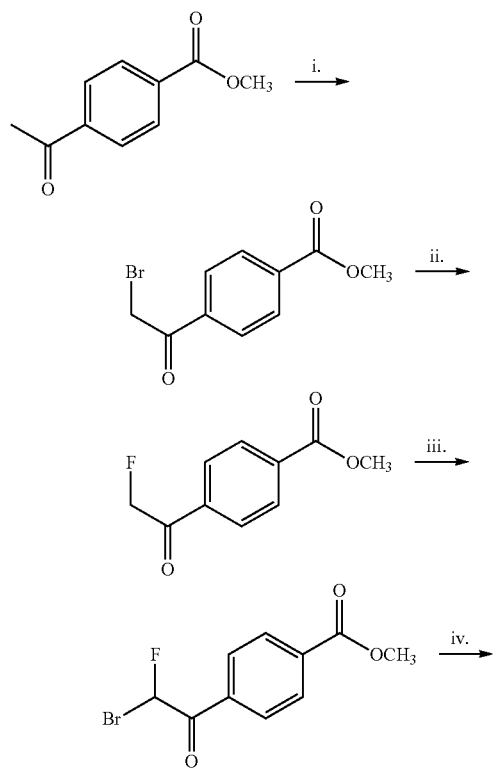

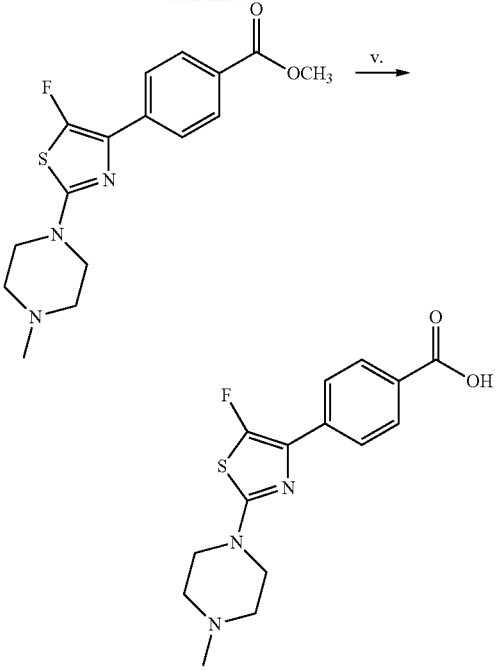

i. AcOH, bromine, RT, 2 h, 55% yield; ii. KF, acetonitrile, 18-crown-6, 90° C., 16 h; 31% yield; iii. AcOH, bromine, 45° C., 4 h, 100% yield; iv. 4-Methyl-piperazine-1-carbothioic acid amide, Δ, 2 h, 74% yield; LiOH, RT, 16 h, 100% yield.

Availability of Starting Materials—

Methyl 4-acetylbenzoate is available from Aldrich; 4-methyl-piperazine-1-carbothioic acid amide—11 suppliers found in SciFinder (for example, Chem Pur Products Ltd in Germany).

Step a) 4-(2-Bromo-acetyl)-benzoic acid methyl ester

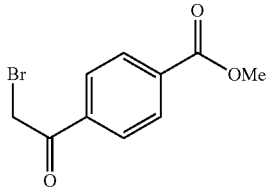 [SMILES: COC(=O)c1ccc(C(=O)CF)cc1]

To a solution of 4-acetyl-benzoic acid methyl ester (8.4 mmol) in acetic acid (20 mL) was added bromine (8.4 mmol). The reaction was stirred at RT for 2 h over which time the red colour disappeared and an off white precipitate formed. The product was collected by filtration and washed with cold methanol/water (200 mL 1:1) to yield a white powder (55%). 1H NMR (400 MHz, CDCl$_3$) 3.98 (3H, s), 4.20 (2H, s), 8.02 (2H, d, J=8 Hz), 8.18 (2H, d, J=8 Hz).

Step b) 4-(2-Fluoro-acetyl)-benzoic acid methyl ester

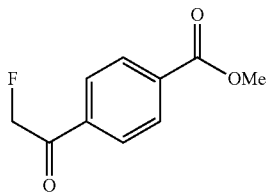

To a suspension of potassium fluoride (3.11 mmol) in acetonitrile (1 mL) was added 18-crown-6 (0.1 mmol) and the reaction was heated at 90° C. for 30 mins. 4-(2-Bromo-acetyl)-benzoic acid (1.56 mmol) was added and the reaction heated at 90° C. for 16 h. The reaction was diluted with water (10 mL) and extracted with ethyl acetate (3×20 mL). The product was purified on silica eluting with 5-15% ethyl acetate in iso-hexane to yield on concentration in vacuo of the desired fractions, the title product as a white solid (31%). 1H NMR (400 MHz, CDCl$_3$) 3.98 (3H, s), 5.55 (2H, d, J=50 Hz), 7.95 (2H, d, J=8 Hz), 8.18 (2H, d, J=8 Hz).

Step c) 4-(2-Bromo-2-fluoro-acetyl)-benzoic acid methyl ester

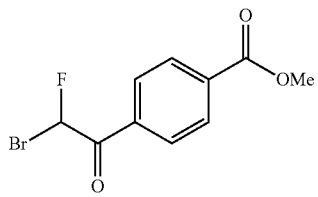 [SMILES: COC(=O)c1ccc(C(=O)C(F)Br)cc1]

To a suspension of 4-(2-fluoro-acetyl)-benzoic acid (1.19 mmol) in acetic acid (5 mL) was added bromine (1.19 mmol). The reaction was heated at 45° C. for 4 h over which time a green solution formed. The reaction was concentrated in vacuo and azeotroped twice with toluene to yield the title compound as a green solid (100%). The product was used crude in the next step.

1H NMR (400 MHz, CDCl$_3$) 3.98 (3H, s), 7.04 (1H, s), 8.05-8.10 (4H, m).

Step d) 4-[5-Fluoro-2-(4-methyl-piperazin-1-yl)-thiazol-4-yl]-benzoic acid methyl ester

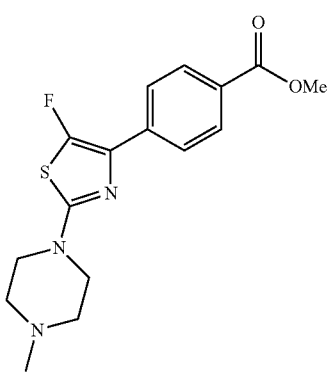 [SMILES: COC(=O)c1ccc(-c2nc(N3CCN(C)CC3)sc2F)cc1]

4-(2-Bromo-2-fluoro-acetyl)-benzoic acid methyl ester (1.18 mmol) and 4-methyl-piperazine-1-carbothioic acid amide (1.18 mmol) were dissolved in ethanol (10 mL). The reaction was heated at reflux for 2 h. The reaction was cooled to RT causing the product to precipitate. The product was collected by filtration and washed with cold ethanol. The product was given an aqueous sodium bicarbonate work up to yield the title compound as a colourless oil (74%). MS (ES+) 337 (M+H, 100%).

Step f) 4-[5-Fluoro-2-(4-methyl-piperazin-1-yl)-thiazol-4-yl]-benzoic acid di-hydrochloride

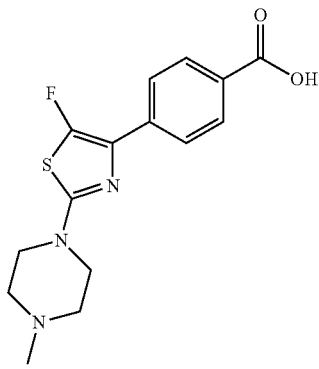 [SMILES: CN1CCN(c2nc(-c3ccc(C(=O)O)cc3)c(F)s2)CC1]

To a solution of 4-[5-fluoro-2-(4-methyl-piperazin-1-yl)-thiazol-4-yl]-benzoic acid methyl ester (0.43 mmol) in tetrahydrofuran/water (2.5 mL, 4:1) was added lithium hydroxide (0.5 mmol). The reaction was stirred at RT for 16 h. The reaction was concentrated in vacuo and hydrochloric acid (2N, 3 mL) was added causing the product to precipitate as a white solid. The product was collected by filtration to yield the title product as a white solid (79%). MS (ES+) 322 (M+H, 100%).

EXAMPLE 12

N-[1-(6-Chloro-3-oxo-hexahydro-furo[3,2-b]pyrrole-4-carbonyl)-3-methyl-butyl]-4-[5-fluoro-2-(4-methyl-piperazin-1-yl)-thiazol-4-yl]-benzamide

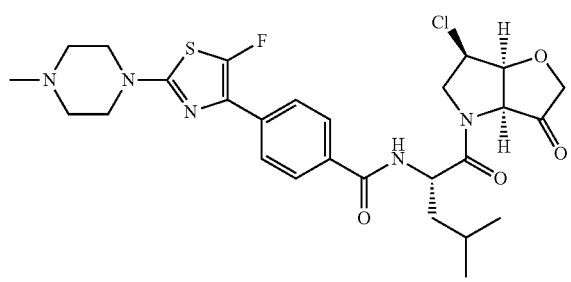 [SMILES: CC(C)C[C@H](NC(=O)c1ccc(-c2nc(N3CCN(C)CC3)sc2F)cc1)C(=O)N1C[C@@H](Cl)[C@H]2OCC(=O)[C@H]21]

Step a) 6-Benzyloxy-3-oxo-hexahydro-furo[3,2-b]pyrrole-4-carboxylic acid benzyl ester (12a)

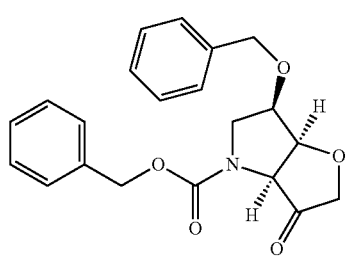 [SMILES: O=C1CO[C@H]2[C@@H]1N(C(=O)OCc1ccccc1)C[C@H]2OCc1ccccc1]

Dess-Martin periodinane (12.5 g, 30 mmol) was dissolved in DCM (250 mL). Compound 10 from WO07/066,180 (7.4 g, 20 mmol) in DCM (50 mL) was added to a stirred solution of oxidant at rt under a nitrogen atmosphere in 45 min Once the reaction was deemed to be complete according to TLC, aqueous 10% Na$_2$S$_2$O$_3$ (200 mL) was added and the mixture was stirred at rt for another 15 minutes. The two phase system was transferred into a separation funnel and extracted twice with EtOAc (200 mL and 100 mL respectively). The combined organic phases were washed once with aqueous saturated NaHCO$_3$ (100 mL) and brine (100 mL), dried over Na$_2$SO$_4$, filtered and the solvent was evaporated in vacuo, yielding the crude product 2 as a clear oil (7.69 g,); ESI$^+$, m/z: 368 (M$^+$+1).

Step b) 6-Benzyloxy-3,3-dimethoxy-hexahydro-furo[3,2-b]pyrrole-4-carboxylic acid benzyl ester (12b)

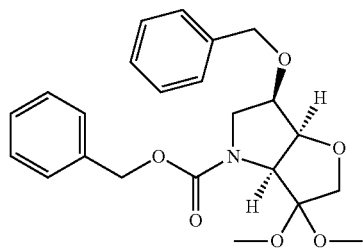 [SMILES: COC1(OC)CO[C@H]2[C@@H]1N(C(=O)OCc1ccccc1)C[C@H]2OCc1ccccc1]

Compound 12a (7.6 g) was dissolved dry methanol (100 mL). Trimethyl orthoformate (30 mL) and pTsOH (0.2 g) was added at rt under a nitrogen atmosphere. The mixture was heated at 60° C. for 8 hours. Once the reaction was deemed complete according to TLC, it was cooled to rt and concentrated in vacuo. The crude product was purified by column chromatography over silica gel eluting with ethyl acetate-heptane (1:4) to afford after concentration in vacuo the ketal 12b as a clear oil (5.9 g, 71% over 2 steps); ESI$^+$, m/z: 382 (M$^+$–OMe).

Step c) (3aS,6R,6aS)-6-Hydroxy-3,3-dimethoxy-hexahydro-furo[3,2-b]pyrrole-4-carboxylic acid tert-butyl ester (12c)

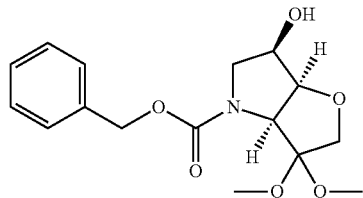 [SMILES: COC1(OC)CO[C@@H]2[C@H](O)CN(C(=O)OCc3ccccc3)[C@@H]21]

A solution of compound 12b (2.5 g, 6.4 mmol) in methanol (60 mL) and Pd(OH)$_2$ (0.7 g) was stirred at rt under H$_2$ atmosphere for 48 hours. The mixture was filtrated and concentrated in vacuo. The residue (2.8 g, 14.8 mmol) was dissolved in 75 mL of a mixture of dioxane/water (2:1). A solution of 10% Na$_2$CO$_3$ (25 mL) was added drop wise to pH 9-9.5. The mixture was cooled to 0° C. in an ice-water bath and Boc anhydride was added in one portion. The reaction was stirred at rt over night and the pH of the mixture was maintained at 9-9.5 by adding more of the 10% solution of Na$_2$CO$_3$ if necessary. The mixture was filtered and the solvent eliminated in vacuo. The aqueous mixture was extracted with 3×100 mL EtOAc, the combined organic phases were washed with 100 mL water and 100 mL brine, dried over Na$_2$SO$_4$, filtered and the solvent was evaporated in vacuo to afford 3.79 g of the carbamate as a clear oil (89%), ESI$^+$, m/z: 312 (M$^+$+Na).

Step d) (3aS,6R,6aS)-6-hydroxy-3,3-dimethoxy-hexahydro-furo[3,2-b]pyrrole-4-carboxylic acid benzyl ester (12d)

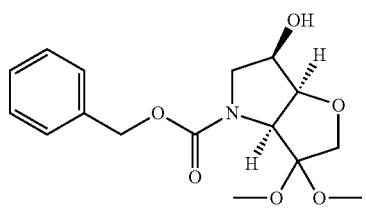 [SMILES: COC1(OC)CO[C@@H]2[C@H](O)CN(C(=O)OCc3ccccc3)[C@@H]21]

To a stirred solution of compound 12c (3.8 g, 13.13 mmol) in CH$_2$Cl$_2$ (100 mL) was added 2M HCl in MeOH (50 mL). The resulting solution was stirred overnight and then concentrated in vacuo and azeotroped with toluene (3×100 mL). The crude residue was dissolved in CH$_2$Cl$_2$ (100 mL) cooled to 0° C. and pyridine (1071 µL, 13.13 mmol) added followed by dropwise addition of CbzCl (1875 µL, 13.13 mmol). The reaction was stirred at room temperature for 2 hours then washed with 2 M HCl (2×50 mL), saturated NaHCO$_3$ (2×50 mL), dried (MgSO$_4$) and concentrated. The residue was purified by flash column chromatography (5-100% isohexane:EtOAc) to obtain the title compound as a clear oil (2510 mg, 59%). MS M+H 324.

Step e (3aS,6R,6aS)-6-Methanesulfonyloxy-3,3-dimethoxy-hexahydro-furo[3,2-b]pyrrole-4-carboxylic acid benzyl ester (12e)

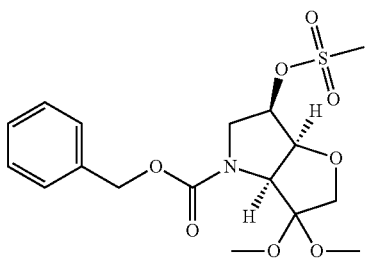 [SMILES: COC1(OC)CO[C@H]2[C@@H]1N(C(=O)OCc1ccccc1)C[C@H]2OS(C)(=O)=O]

To a stirred solution of compound 12d (500 mg, 1.55 mmol) in CH$_2$Cl$_2$ (20 mL) was added triethyl amine (332 µL, 2.32 mmol) and mesyl chloride (266 mg, 2.32 mmol). After stirring for 30 minutes the reaction was washed with saturated NaHCO$_3$ (1×20 mL), 2M HCl (1×20 m), dried MgSO$_4$ and concentrated to give the title compound (655 mg, 99%) as a yellow oil. MS M+H 402.

Step f (3aS,6S,6aS)-6-Chloro-3,3-dimethoxy-
hexahydro-furo f[3,2-b]pyrrole-4-carboxylic acid
benzyl ester (12f)

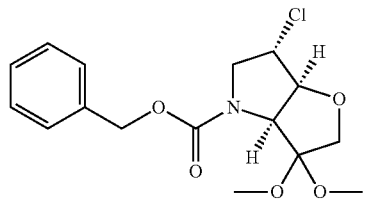 [SMILES: COC1(OC)CO[C@H]2[C@@H]1N(C(=O)OCc1ccccc1)C[C@@H]2Cl]

To a stirred solution of compound 12e (550 mg, 1.37 mmol) in DMF (30 mL) was added lithium chloride (721 mg, 13.7 mmol). After stirring for 120 minutes at 120° C. the reaction was concentrated in vacuo. The residue was diluted with CH$_2$Cl$_2$ (50 mL) washed with water (1×20 mL), dried with MgSO$_4$ and concentrated in vacuo. The residue was purified by flash column chromatography (5-66% isohexane: EtOAc) to give the title compound (330 mg, 72%) as a yellow oil. MS M+H 342, 344.

Step g) [2-(6-Chloro-3,3-dimethoxy-hexahydrofuro
[3,2-b]pyrrole-4-carbonyl)-3-methylbutyl]-carbamic
acid tertbutyl ester (12g)

6-Chloro-3,3-dimethoxy-hexahydro-furo[3,2-b]pyrrole-4-carboxylic acid benzyl ester (68 mg, 0.20 mmol) was deprotected by catalytic hydrogenation using 10% palladium on charcoal and hydrogen under atmospheric pressure. After stirring for 2 hours, the suspension was filtered through Celite and the filtrate evaporated on rotavapor to give the crude 6-chloro-3,3-dimethoxy-hexahydrofuro[3,2-b]pyrrole, which was coupled with N-Boc-leucine using HATU in the same way as the method described in Example 2, which gave the title compound (78 mg, 93%). MS m/z 421.2 (M+H)$^+$.

Step h) N-[2-(6-Chloro-3,3-dimethoxy-hexahydro-
furo[3,2-b]pyrrole-4-carbonyl)-3-methylbutyl]-4-[5-
fluoro-2-(4-methyl-piperazin-1-yl)-thiazol-4-yl]-
benzamide (12h)

[2-(6-Chloro-3,3-dimethoxy-hexahydrofuro[3,2-b]pyrrole-4-carbonyl)-3-methylbutyl]-carbamic acid tertbutyl ester (78 mg, 0.185 mmol) was deprotected under acidic conditions (acetyl chloride in methanol) as described in Example 4, and the crude pyrrole hydrochloride intermediate was then coupled with the HCl salt of 4-[5-fluoro-2-(4-methyl-piperazin-1-yl)-thiazol-4-yl]-benzoic acid using the HATU conditions as described in Example 2, which gave the title compound (98 mg, 85%). MS m/z 624.2 (M+H)$^+$.
$^1$H-NMR (400 MHz, CDCl$_3$): 7.91 (d, 2H), 7.81 (d, 2H), 6.85 (d, 1H), 5.00 (m, 1H), 4.75 (d, 1H), 4.60 (m, 1H), 4.50 (dt, 1H), 4.12 (d, 1H), 3.92 (d, 1H), 3.75 (m, 1H), 3.49 (m, 4H), 3.48 (m, 1H), 3.45 (s, 3H), 128 (s, 3H), 2.62 (m, 4H), 2.42 (s, 3H), 1.85 (m, 1H), 1.70 (m, 2H), 1.05 (d, 3H), 1.00 (d, 3H).

Step i) N-[1-(6-Chloro-3-oxo-hexahydro-furo[3,2-b]
pyrrole-4-carbonyl)-3-methyl-butyl]-4-[5-fluoro-2-
(4-methyl-piperazin-1-yl)-thiazol-4-yl]-benzamide
(12i)

N-[2-(6-Chloro-3,3-dimethoxy-hexahydrofuro[3,2-b]pyrrole-4-carbonyl)-3-methylbutyl]-4-[5-fluoro-2-(4-methylpiperazin-1-yl)-thiazol-4-yl]-benzamide (98 mg, 0.157 mmol) was hydrolyzed under acidic conditions as described in Example 5. The residue was purified by preparative HPLC chromatography (C8, gradient 10-90% MeCN/H$_2$O) which gave pure title compound 41.8 mg (46%), as a mixture of 2 rotamers of both the ketone (27%) [MS m/z 578.1 (M+H)$^+$] and the hydrate (73%) [MS m/z 596.1 (M+H$_2$O+H)$^+$].

EXAMPLE 13

6-Chloro-4-{4-methyl-2-[2,2,2-trifluoro-1-(4'-meth-
anesulfonyl-biphenyl-4-yl)-ethylamino]-pentanoyl}-
tetrahydro-furo[3,2-b]pyrrol-3-one

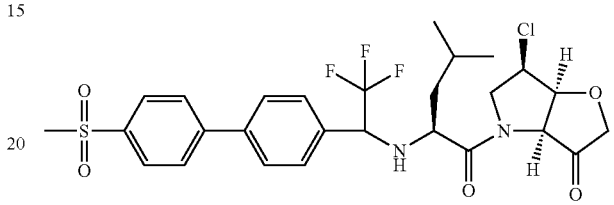

Step a 1-(6-Chloro-3,3-dimethoxy-hexahydro-furo[3,
2-b]pyrrol-4-yl)-4-methyl-2-[2,2,2-trifluoro-1-(4'-
methanesulfonyl-biphenyl-4-yl)-ethylamino]-pentan-
1-one (13a)

6-Chloro-3,3-dimethoxy-hexahydro-furo[3,2-b]pyrrole-4-carboxylic acid benzyl ester (55 mg, 0.16 mmol) was deprotected by catalytic hydrogenation using 10% palladium on charcoal and hydrogen under atmospheric pressure. After stirring for 2 hours, the suspension was filtered through Celite and the filtrate was concentrated, The afforded amine was then coupled with 4-methyl-2-[2,2,2-trifluoro-1-(4'-methanesulfonyl-biphenyl-4-yl)-ethylamino]-pentanoic acid (76 mg, 0.17 mmol), prepared as described in WO07/006716, using the HATU conditions as described in Example 2, which gave the title compound (101 mg, 50%).

Step b

Compound 13a (47 mg, 0.07 mmol) was hydrolyzed under acidic conditions as described in Example 5. The afforded residue was purified by column chromatography (EtOAc-P.ether 3:2) which gave pure title compound (26 mg), [MS m/z 586.4.

EXAMPLE 14

6-Chloro-4-[4-methyl-2-(2,2,2-trifluoro-1-{4-[2-(4-
methyl-piperazin-1-yl)-thiazol-4-yl]-phenyl}-ethy-
lamino)-pentanoyl]-tetrahydro-furo[3,2-b]pyrrol-3-
one

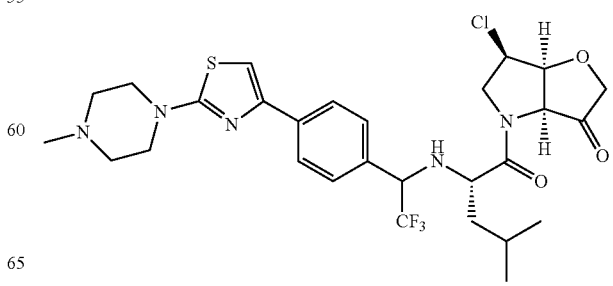

Step a) 1-(6-Chloro-3,3-dimethoxy-hexahydro-furo[3,2-b]pyrrol-4-yl)-4-methyl-2-(2,2,2-trifluoro-1-{4-[2-(4-methyl-piperazin-1-yl)-thiazol-4-yl]-phenyl}-ethylamino)-pentan-1-one (14a)

The benzyl group of 6-chloro-3,3-dimethoxy-hexahydro-furo[3,2-b]pyrrole-4-carboxylic acid benzyl ester (35 mg, 0.10 mmol) was removed by catalytic hydrogenation using 10% palladium on charcoal and hydrogen under atmospheric pressure. After stirring for 2 hours, the suspension was filtered through Celite and the filtrate was concentrated, The afforded amine was then coupled with the acid of Example 11, step d (42 mg, 0.09 mmol) using the HATU conditions as described in Example 2, which gave the title compound (45 mg).

Step b

Compound 14a (47 mg, 0.07 mmol) was hydrolyzed under acidic conditions as described in Example 5. The afforded residue was purified by column chromatography (CH$_2$Cl$_2$-aceton 2:1+0.05% DIEA) which gave pure title compound (20 mg).

EXAMPLE 15

Alternative synthesis of P1 building block

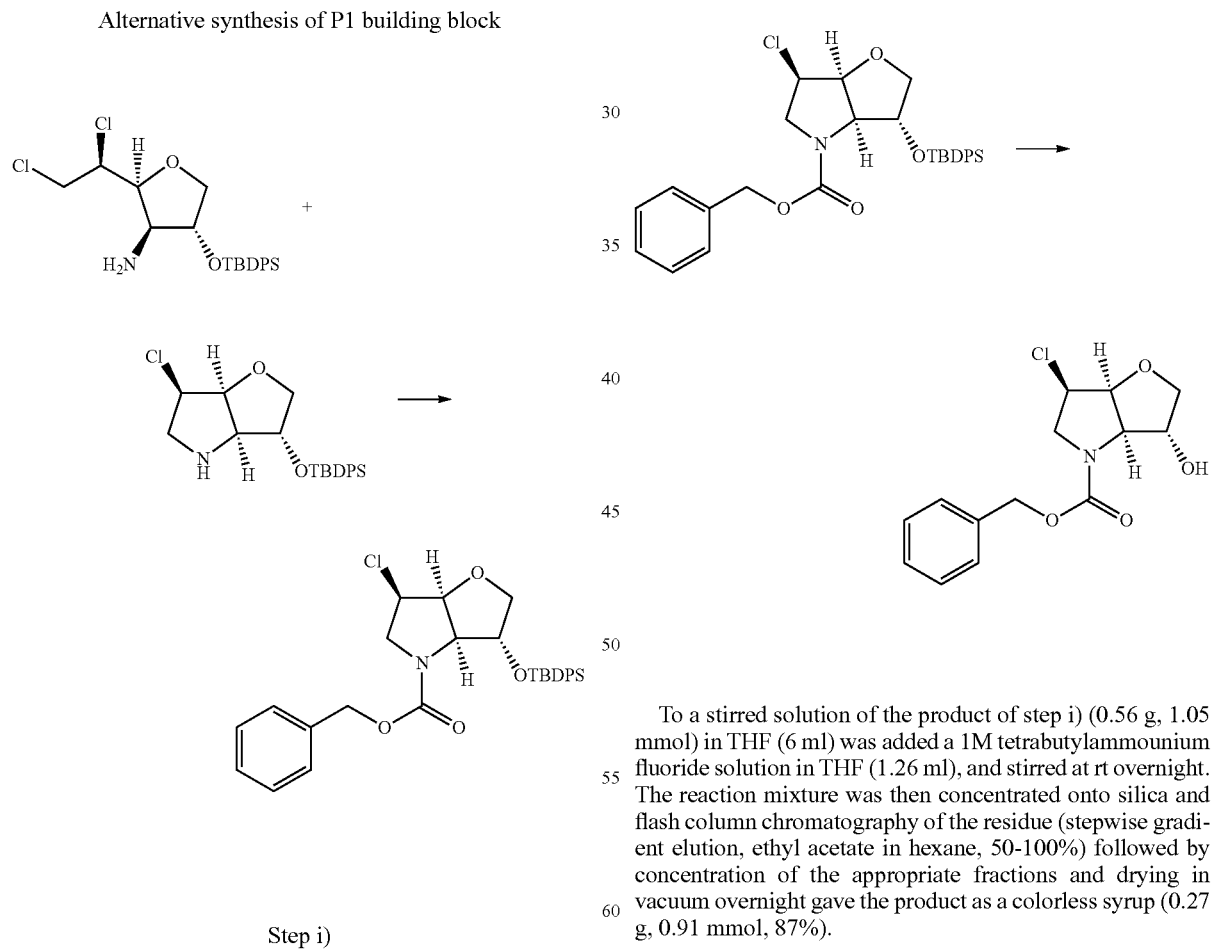

Step i)

Step g) of Example 1 was optimised as follows: A mixture of the above depicted mono- and bicyclic amines (approx 1.8 mmol) from the first reaction of step g) was dissolved in ethyl acetate (25 ml) and triethyl amine (1.5 ml) was added. The solution was refluxed for 3 h, monitored by LC-MS, then additional triethyl amine (1.5 ml) was added and the reaction mixture was refluxed another 15 h. The reaction mixture was then cooled to approximately 0° C. and benzyl chloroformate (0.38 ml, 2.7 mmol) was added in one portion then allowed to reach rt. The reaction was monitored by TLC (4:1 and 3:2 hexane-ethylacetate, visualized by UV-light and AMC-staining) and after 4 h the reaction mixture was diluted with ethyl acetate (15 ml), washed successively with aq. 10% citric acid (3×25 ml) and aq. saturated sodium hydrogen carbonate (3×25 ml), then dried (sodium sulfate), filtered and concentrated. Flash chromatography of the residue (stepwise gradient elution, ethyl acetate in hexane, 10-20%) followed by concentration of the appropriate fractions and drying in vacuum overnight gave the product as a colorless foam (0.57 g, 1.06 mmol).

NMR data (400 MHz, 298 K, CDCl$_3$): $^1$H, □ 1.02 and 1.10 (2 s, 9H, C(CH$_3$)$_3$), 3.13 (m, 1H, CHH), 3.59 and 3.80 (2 m, 2×1H, CH$_2$), 3.99-4.15 (m, 2H, CHH and CH), 4.34, 4.42, 4.46 and 4.68 (4 brs, 2H, major and minor CH), 4.84 (m, 1H, CH), 4.92-5.16 (m, 2H, CH$_2$), 7.11-7.80 (m, 15H, ArH).

Step ii)

To a stirred solution of the product of step i) (0.56 g, 1.05 mmol) in THF (6 ml) was added a 1M tetrabutylammounium fluoride solution in THF (1.26 ml), and stirred at rt overnight. The reaction mixture was then concentrated onto silica and flash column chromatography of the residue (stepwise gradient elution, ethyl acetate in hexane, 50-100%) followed by concentration of the appropriate fractions and drying in vacuum overnight gave the product as a colorless syrup (0.27 g, 0.91 mmol, 87%).

NMR data (400 MHz, 298 K, CDCl$_3$): $^1$H, □ 2.22 and 3.00 (2 d, 1H, J$_{OH,3}$=3.5 Hz, OH major and minor), 3.30 (m, 1 H, CHH), 3.89 (m, 1H, CHH), 4.00-4.16 (m, 3H, 2 CHH and CH), 4.24 (d, 1H, CH), 4.43 and 4.54 (2 brs, 1H, H-3 major and minor), 4.70 (m, 1H, CH), 5.08-5.23 (m, 2H, OCH$_2$Ph), 7.32-7.40 (m, 5H, Ar—H).

Step iii)

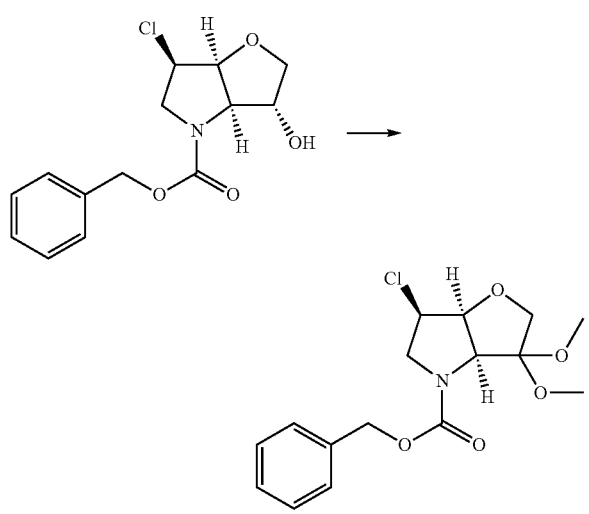

To a stirred solution of the product of step ii) (0.26 g, 0.88 mmol) in dichloromethane (6 ml) was added Dess-Martin periodinane (0.41 g, 0.97 mmol) at rt. The reaction was monitored by TLC (3:2 ethyl acetate-hexane, visualized by staining with AMC) and after 3.5 h the reaction mixture was diluted with dichloromethane (20 ml), washed with 1:1 aq. saturated sodium hydrogen carbonate/aq. 10% sodium thiosulfate (3×20 ml), then dried (sodium sulfate), filtered and concentrated. The residue was redissolved in methanol (5 ml) and trimethyl orthoformate (1.25 ml) and p-toluenesulphonic acid mono hydrate (0.03 g, 0.16 mmol) was added. The reaction mixture was kept at 60° C. overnight, then diisopropyl ethylamine (0.5 ml) was added and the reaction mixture was concentrated. Flash chromatography (stepwise gradient elution, ethyl acetate in hexane, 20-40%) of the residue followed by concentration of the appropriate fractions and drying in vacuum over the weekend gave the product as a colorless hard syrup (0.27 g, 0.79 mmol, 89%).

NMR data (400 MHz, 298 K, CDCl$_3$): $^1$☐.☐3.08-3.47 (m, 7H, 2×OCH$_3$ major and minor and CHH), 3.80 (m, 2H, CH$_2$), 3.98 (brs, 1H, CH), 4.25 (m, 1H, CHH), 4.45 (m, 1H, CH), 4.60 (t, 1H, CH), 5.04-5.26 (m, 2H, CH$_2$), 7.29-7.42 (m, 5H, Ar—H)

COMPARATIVE EXAMPLE 1

N-[(S)-1-((3aS,6S,6aS)-6-chloro-3-oxo)-hexahydro-furo[3,2-b]pyrrole-4-carbonyl)-3-methyl-butyl]-4-[2-(4-methyl-piperazin-1-yl)-thiazol-4-yl]benzamide

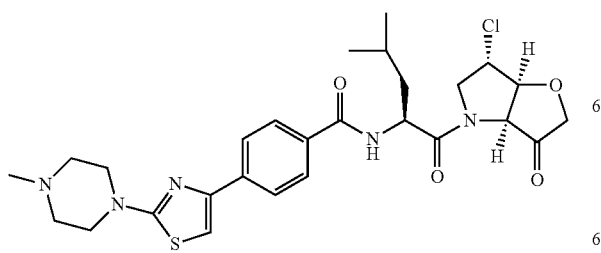

The 6-S chloro building block was prepared as shown in the scheme below:

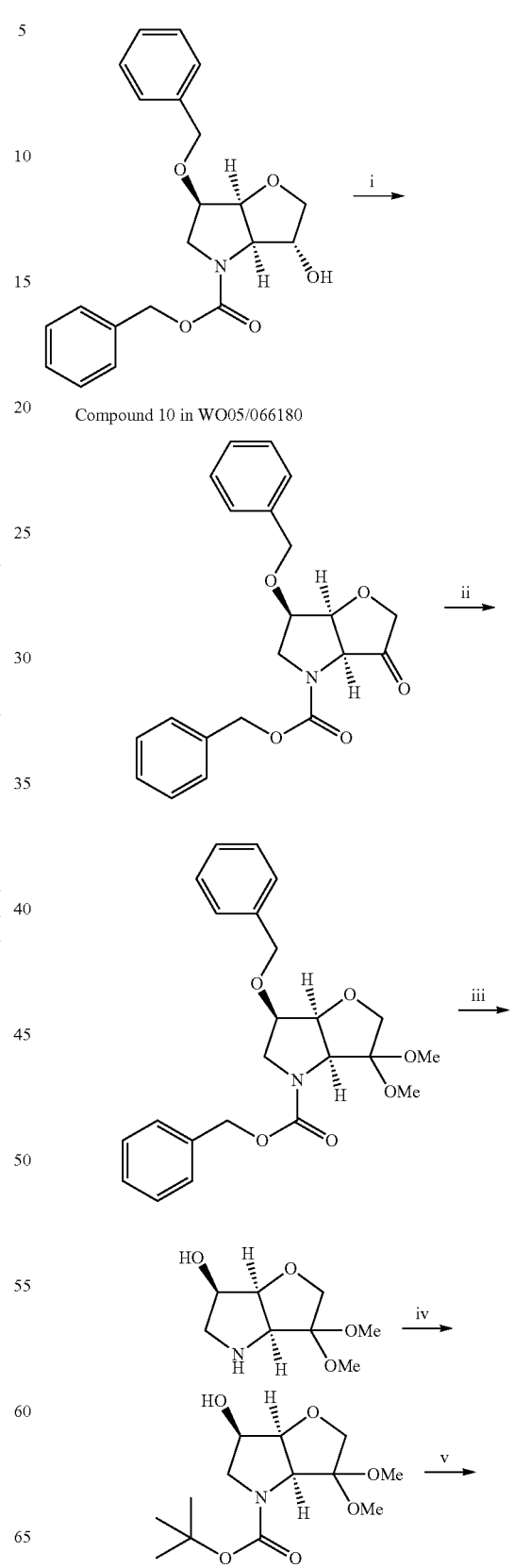

Compound 10 in WO05/066180

-continued

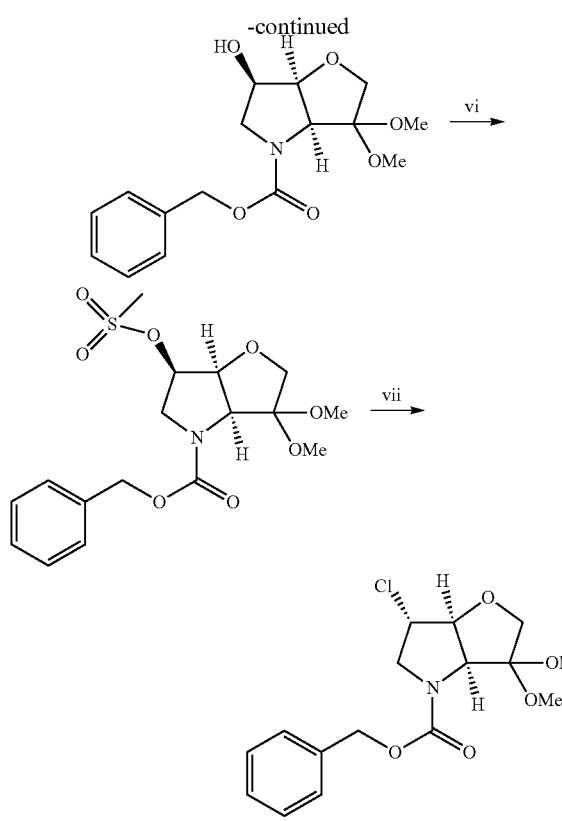

i. Dess-Martin Periodinane, DCM, 2 h, RT;
ii. Trimethylorthoformate, pTsOH, MeOH, 8 h, 60° C.;
iii. Pd(OH)₂, H₂, MeOH, 48 h, RT;
iv. Boc₂O, 10% Na₂CO₃, 16 h, 0° C. to RT;
v. HCl, CH₂CH₂/Py, CBzCl
vi. CH₂CH₂/Et₃N MsCl
vii DMF, LiCl This building block was then N-deprotected and taken through the remainder of the synthesis as described in Example 5 to afford N-[(S)-1-((3aS,6aS)-6R-chloro-3-oxo)-hexahydro-furo[3,2-b]pyrrole-4-carbonyl)-3-methyl-butyl]-4-[2-(4-methyl-piperazin-1-yl)-thiazol-4-yl]benzamide.

COMPARATIVE EXAMPLE 2

N-[(S)-1-((3aS,6aR)-3-oxo)-hexahydro-furo[3,2-b]pyrrole-4-carbonyl)-3-methyl-butyl]-4-[2-(4-methyl-piperazin-1-yl)-thiazol-4-yl]benzamide

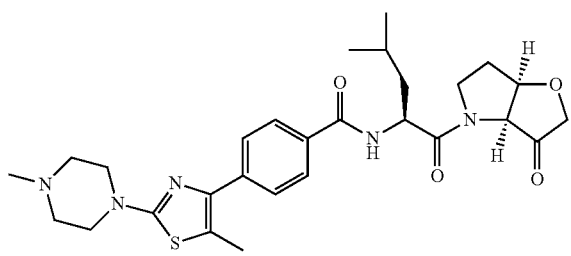 [SMILES: Cc1sc(N2CCN(C)CC2)nc1-c1ccc(C(=O)N[C@@H](CC(C)C)C(=O)N2CC[C@H]3OCC(=O)[C@H]32)cc1]

The P1 building block was synthesised as described in WO02/05720, coupled to N-protected L-leucine and the P3 building block of Example 3 above, and oxidised to the ketone as shown in Example 4.

COMPARATIVE EXAMPLE 3

N-[(S)-1-((3aS,6aR)-3-oxo)-hexahydro-furo[3,2-b]pyrrole-4-carbonyl)-3-methyl-butyl]-4-[2-(4-methyl-piperazin-1-yl)-thiazol-4-yl]benzamide

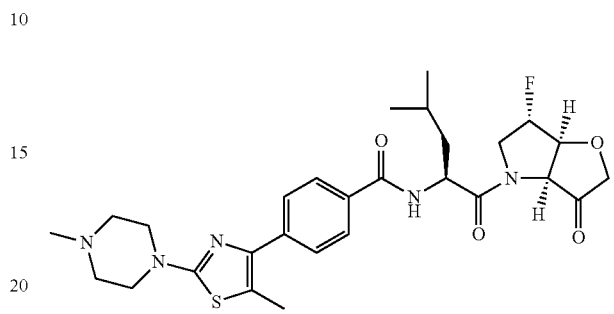

The synthesis of this comparative example is shown as Example 9 of WO05/66180.

BIOLOGICAL EXAMPLES

Determination of cathepsin K proteolytic catalytic activity

Convenient assays for cathepsin K are carried out using human recombinant enzyme, such as that described in PDB.
ID BC016058 standard; mRNA; HUM; 1699 BP.
DE *Homo sapiens* cathepsin K (pycnodysostosis), mRNA (cDNA clone MGC:23107
RX MEDLINE; RX PUBMED; 12477932.
DR RZPD; IRALp962G1234.
DR SWISS-PROT; P43235;

The recombinant cathepsin K can be expressed in a variety of commercially available expression systems including *E. coli*, *Pichia* and Baculovirus systems. The purified enzyme is activated by removal of the prosequence by conventional methods.

Standard assay conditions for the determination of kinetic constants used a fluorogenic peptide substrate, typically H-D-Ala-Leu-Lys-AMC, and were determined in either 100 mM Mes/Tris, pH 7.0 containing 1 mM EDTA and 10 mM 2-mercaptoethanol or 100 mMNa phosphate, imM EDTA, 0.1% PEG4000 pH 6.5 or 100 mM Na acetate, pH 5.5 containing 5 mM EDTA and 20 mM cysteine, in each case optionally with 1M DTT as stabiliser. The enzyme concentration used was 5 nM. The stock substrate solution was prepared at 10 mM in DMSO. Screens were carried out at a fixed substrate concentration of 60 µM and detailed kinetic studies with doubling dilutions of substrate from 250 µM. The total DMSO concentration in the assay was kept below 3%. All assays were conducted at ambient temperature. Product fluorescence (excitation at 390 nm, emission at 460 nm) was monitored with a Labsystems Fluoroskan Ascent fluorescent plate reader. Product progress curves were generated over 15 minutes following generation of AMC product.

Cathepsin S Ki determination

The assay uses baculovirus-expressed human cathepsin S and the boc-Val-Leu-Lys-AMC fluorescent substrate available from Bachem in a 384 well plate format, in which 7 test compounds can be tested in parallel with a positive control comprising a known cathepsin S inhibitor comparator.

Substrate Dilutions

280 μl/well of 12.5% DMSO are added to rows B-H of two columns of a 96 deep well polypropylene plate. 70 μl/well of substrate is added to row A. 2×250 μl/well of assay buffer (100 mM Na phosphate, 100 mM NaCl, pH 6.5) is added to row A, mixed, and double diluted down the plate to row H.
Inhibitor Dilutions.

100 μl/well of assay buffer is added to columns 2-5 and 7-12 of 4 rows of a 96 well V bottom polypropylene plate. 200 μl/well of assay buffer is added to columns 1 and 6.

The first test compound prepared in DMSO is added to column 1 of the top row, typically at a volume to provide between 10 and 30 times the initially determined rough $K_i$. The rough Ki is calculated from a preliminary run in which 10 μl/well of 1 mM boc-VLK-AMC (1/10 dilution of 10 mM stock in DMSO diluted into assay buffer) is dispensed to rows B to H and 20 μl/well to row A of a 96 well Microfluor™ plate. 2 μl of each 10 mM test compound is added to a separate well on row A, columns 1-10. Add 90 μl assay buffer containing 1 mM DTT and 2 nM cathepsin S to each well of rows B-H and 180 μl to row A. Mix row A using a multichannel pipette and double dilute to row G. Mix row H and read in the fluorescent spectrophotometer.

The readings are Prism data fitted to the competitive inhibition equation, setting S=100 μM and $K_M$=100 μM to obtain an estimate of the $K_i$, up to a maximum of 100 μM.

The second test compound is added to column 6 of the top row, the third to column 1 of the second row etc. Add 1 μl of comparator to column 6 of the bottom row. Mix column 1 and double dilute to column 5. Mix column 6 and double dilute to column 10.

Using an 8-channel multistepping pipette set to 5×10 μl, distribute 10 μl/well of substrate to the 384 well assay plate. Distribute the first column of the substrate dilution plate to all columns of the assay plate starting at row A. The tip spacing of the multichannel pipette will correctly skip alternate rows. Distribute the second column to all columns starting at row B.

Using a 12-channel multistepping pipette set to 4×10 μl, distribute 10 μl/well of inhibitor to the 384 well assay plate. Distribute the first row of the inhibitor dilution plate to alternate rows of the assay plate starting at A1. The tip spacing of the multichannel pipette will correctly skip alternate columns. Similarly, distribute the second, third and fourth rows to alternate rows and columns starting at A2, B1 and B2 respectively.

Mix 20 ml assay buffer and 20 μl 1M DTT. Add sufficient cathepsin S to give 2 nM final concentration.

Using the a distributor such as a Multidrop 384, add 30 μl/well to all wells of the assay plate and read in fluorescent spectrophotomoter such as an Ascent.

Fluorescent readings, (excitation and emission wavelengths 390 nm and 460 nm respectively, set using bandpass filters) reflecting the extent of enzyme cleavage of the fluorescent substrate, notwithstanding the inhibitor, are linear rate fitted for each well.

Fitted rates for all wells for each inhibitor are fitted to the competitive inhibition equation using SigmaPlot 2000 to determine V, Km and Ki values.
Cathepsin L Ki The procedure above with the following amendments is used for the determination of Ki for cathepsin L.

The enzyme is commercially available human cathepsin L (for example Calbiochem). The substrate is H-D-Val-Leu-Lys-AMC available from Bahcem. The assay buffer is 100 mM sodium acetate 1 mM EDTA, pH5.5) The DMSO stock (10 mM in 100% DMSO) is diluted to 10% in assay buffer. Enzyme is prepared at 5 nM concentration in assay buffer plus 1 mM dithiothreitol just before use. 2 ul of 10 mM inhibitor made up in 100% DMSO is dispensed into row A. 10 ul of 50 uM substrate (=1/200 dilution of 10 mM stock in DMSO, diluted in assay buffer)
Inhibition Studies Potential inhibitors are screened using the above assay with variable concentrations of test compound. Reactions were initiated by addition of enzyme to buffered solutions of substrate and inhibitor. $K_i$ values were calculated according to equation 1

$$v_0 = \frac{VS}{K_M\left(1 + \frac{I}{K_i}\right) + S} \quad (1)$$

where $v_o$ is the velocity of the reaction, V is the maximal velocity, S is the concentration of substrate with Michaelis constant of $K_M$, and I is the concentration of inhibitor.

Results are presented as
A under 50 nanomolar
B 50-500 nanomolar
C 501-1000 nanomolar
D 1001-5000 nanomolar
E 5001-10 000 nanomolar
F in excess of 10 000 nanomolar

TABLE 1

| Example | Ki cathepsin K | Ki cathepsin S | Ki cathepsin L |
| --- | --- | --- | --- |
| 5 | A | E | C |
| 6 | A | D | C |
| 7 | A | D | D |
| 8 | A | F | D |
| 10 | A | D | B |
| 12 | A | F | D |
| 13 | A | F | D |

The compounds of formula II are thus potent inhibitors of cathepsin K and yet selective over the closely related cathepsin S and L.

Representative values from specific batches of compound/enzyme/assay occasion include:

| Example | Ki cathepsin K | Ki cathepsin S | Ki cathepsin L |
| --- | --- | --- | --- |
| 5 | 1.6 | 7500 | 880 |
| 6 | 1.5 | 4000 | 890 |
| 7 | 4.2 | 1700 | 1200 |
| 8 | 3.3 | 13000 | 2900 |
| 10 | 3.4 | 4700 | 490 |
| 12 | 1.8 | 11000 | 1600 |

Metabolic Stability

Compounds of the invention and the indicated comparative examples were tested for metabolic stability in a cytosol assay in which the compounds were incubated with commercially available human hepatic cytosol fractions and the disappearance of the compound monitored by HPLC or LC/MS. Pooled human liver cytosol fractions are less likely to represent outlier individuals than blood from a single individual and can be stored frozen, unlike whole blood. The cytosol assay thus provides a consistent assay testbed as a guide to the stability of a compound in the in vivo environment, such as when exposed to whole blood.

In short, test compounds (2 μM) are incubated in pooled human liver cytosol (Xenotech LLC Lenexa US, 1 mg/mL protein in 0.1M phosphate buffer, pH 7.4) at 37° centigrade over a one hour period. The incubations are initiated by the addition of 1 mM NADPH co-factor. Timed sub-samples were taken at 0, 20, 40 and 60 minutes and "crash precipitated" by the addition of 3 volumes of ice-cold acetonitrile. The samples were centrifuged at reduced temperature and the supernatants were separated and analyzed by LC-MS-MS.

Alternatively, an analogous stability assay is carried out in human or monkey whole blood.

Comparative example 3 employs the down-F epimer of the P1 unit of WO0566180. Comparative example 2 employs the preferred P1 and P2 units of WO02/057270 together with a P3 unit within the scope of the present claims (which are outside the scope of WO02/057270). Comparative example 1 shows the down-Cl epimer of the compound of Example 6.

TABLE 2

| Example | | $t_{1/2}$ minutes |
|---|---|---|
| Comparative Example 2 | | 72 |
| Comparative Example 3 | | 100-150 |
| Comparative Example 1 | | 24 |
| Example 6 | | >300 |
| Example 5 | | 198 |
| Example 11 | | 180 |

TABLE 2-continued

| Example | | $t_{1/2}$ minutes |
|---|---|---|
| Example 12 | [chemical structure] | 270 |

It will be apparent from comparative example 2 that the prior art P1 of WO02/057270 provides compounds with a cytosol half life of a little over an hour. The down fluoro P1 extensively exemplified in WO05/66180 is somewhat better with a half life in excess of 1½ hours. However, substitution of chloro for the down-fluoro of WO05/66180 dramatically reduces the stability as illustrated by comparing comparative example 1 with comparative example 3. In contrast, the up-chloro epimer of the invention (example 6) has provided a compound with a half life in in excess of 5 hours. Similarly, with an identical P3 and P2 component, comparative example 2 and the up-chloro epimer of the invention (example 5) clearly demonstrates that the up-chloro epimer provides a much improved half life.

Permeability

This example measures transport of inhibitors through the cells of the human gastroenteric canal. The assay uses the well known Caco-2 cells with a passage number between 40 and 60.

Apical to Basolateral Transport

Generally every compound will be tested in 2-4 wells. The basolateral and the apical wells will contain 1.5 mL and 0.4 mL transport buffer (TB), respectively, and the standard concentration of the tested substances is 10 μM. Furthermore all test solutions and buffers will contain 1% DMSO. Prior to the experiment the transport plates are pre-coated with culture medium containing 10% serum for 30 minutes to avoid nonspecific binding to plastic material. After 21 to 28 days in culture on filter supports the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes" and the remaining row unassigned.

The culture medium from the apical wells is removed and the inserts are transferred to a wash row (No. 1) in a transport plate (plate no. 1) out of 2 plates without inserts, which have already been prepared with 1.5 mL transport buffer (HBSS, 25 mM HEPES, pH 7.4) in rows 1 to 5. In A→B screening the TB in basolateral well also contains 1% Bovine Serum Albumin.

0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 μL TB (pH 6.5), including the test substance is added to the apical (donor) well. The plates are incubated in a polymix shaker at 37° C. with a low shaking velocity of approximately 150 to 300 rpm.

After 30 minutes incubation in row 2 the inserts will be moved to new pre-warmed basolateral (receiver) wells every 30 minutes; row 3 (60 minutes), 4 (90 minutes) and 5 (120 minutes).

25 μL samples will be taken from the apical solution after ~2 minutes and at the end of the experiment. These samples represent donor samples from the start and the end of the experiment.

300 μL will be taken from the basolateral (receiver) wells at each scheduled time point and the post value of TEER is measured at the end the experiment. To all collected samples acetonitrile will be added to a final concentration of 50% in the samples. The collected samples will be stored at −20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 μM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 μL fresh TB, pH 6.5 is added to the inserts. After 30 minutes 250 μL is withdrawn from the apical (receiver) well and replaced by fresh transport buffer. Thereafter 250 μL samples will be withdrawn and replaced by fresh transport buffer every 30 minutes until the end of the experiment at 120 minutes, and finally a post value of TEER is measured at the end of the experiment. A 25 μL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum \frac{C_{RI}}{C_{DI}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate (min$^{-1}$) defined as the slope obtained by linear regression of cumulative fraction absorbed ($FA_{cum}$) as a function of time (min), $V_R$ is the volume in the receiver chamber (mL), and A is the area of the filter (cm$^2$).

Typical Reference Compounds:

| Category of absorption in man | Markers | % absorption in man |
|---|---|---|
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

Representative results for compounds of the invention in this Caco-2 assay include Papp values of 5.2×10$^6$ for the compound of Example 10 and 10×10$^6$ cm/sec for the compound of Example 12. Compounds of Formula IB comprising a trifluoromethyl group such as Example 13 generally have Papp values 2-5 fold higher.

Abbreviations

| | | | |
|---|---|---|---|
| DMF | dimethylformamide | DCM | dichloromethane |
| TBDMS | tert-butyldimethylsilyl | RT | room temperature |
| THF | tetrahydrofuran | Ac | acetyl |
| TLC | thin layer chromatography | DMAP | dimethylaminopyridine |
| EtOAc | ethyl acetate | | |

All references referred to in this application, including patents and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A method for the treatment of osteoarthritis, comprising administration of an effective amount of a compound of the formula:

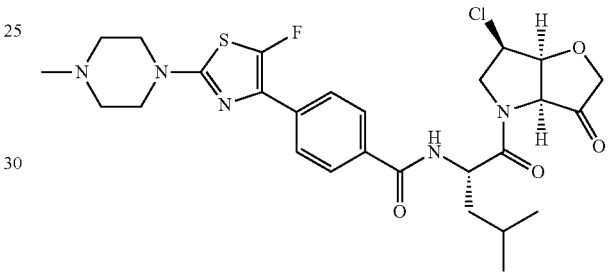

or a pharmaceutically acceptable salt, hydrate or N-oxide thereof to a subject in need thereof.

2. A method for the treatment of osteoarthritis, comprising administration of an effective amount of a compound of the formula:

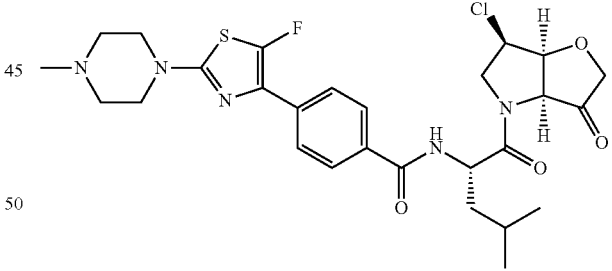

to a subject in need thereof.

* * * * *